United States Patent
Allred et al.

(10) Patent No.: US 7,056,118 B2
(45) Date of Patent: *Jun. 6, 2006

(54) COMPOSITIONS AND DEVICES HAVING A TRAY-LIKE CONFIGURATION FOR DELIVERING A MEDICAMENT AND METHODS OF MANUFACTURING AND USING SUCH COMPOSITIONS AND DEVICES

(75) Inventors: Peter M. Allred, Riverton, UT (US); Neil T. Jessop, Sandy, UT (US)

(73) Assignee: Ultradent Products, Inc., South Jordan, UT (US)

( * ) Notice: Subject to any disclaimer, the term of this patent is extended or adjusted under 35 U.S.C. 154(b) by 375 days.

This patent is subject to a terminal disclaimer.

(21) Appl. No.: 10/646,484

(22) Filed: Aug. 22, 2003

(65) Prior Publication Data
US 2004/0241619 A1    Dec. 2, 2004

Related U.S. Application Data

(63) Continuation-in-part of application No. 10/637,237, filed on Aug. 8, 2003, which is a continuation-in-part of application No. 10/446,235, filed on May 27, 2003, and a continuation-in-part of application No. 10/446,471, filed on May 27, 2003.

(51) Int. Cl.
*A61C 15/00* (2006.01)
*A61K 9/20* (2006.01)

(52) U.S. Cl. .......................... 433/215; 424/53
(58) Field of Classification Search .................. 433/80, 433/215, 216; 424/53; 206/63.5, 369
See application file for complete search history.

(56) References Cited

U.S. PATENT DOCUMENTS 165,584 A    7/1875    Hopfen (Continued)

FOREIGN PATENT DOCUMENTS

WO    WO 88/06869    9/1988

(Continued)

OTHER PUBLICATIONS

Technical Bulletin: Hydrogen Peroxide-Polyvinylpyrrolidone Polymer Complexes, International Specialty Products, 1361 Alps Road, Wayne New Jersey 07470, www.ispcorp.com (Dec. 2003).

*Primary Examiner*—Todd E. Manahan
(74) *Attorney, Agent, or Firm*—Workman Nydegger

(57) ABSTRACT

Medicament compositions are in the shape of a dental tray or tray-like configuration, optionally in combination with a protective barrier layer. Shaped medicament compositions comprise a substantially solid medicament layer that has increased adhesiveness to teeth and/or gingiva when moistened with saliva or water. The shape of the medicament composition facilitates placement of the composition over a person's teeth and/or gingiva with substantially less manipulation compared to the use of initially flat strips. The substantially solid medicament composition becomes more adhesive when moistened with saliva or water, yet remains intact and coherent after the medicament composition is placed over a person's teeth and/or gingiva, particularly when used in combination with a moisture-resistant barrier. The result is that the moistened medicament composition is able to reliably adhere against a user's teeth and/or gingiva during a treatment procedure.

68 Claims, 7 Drawing Sheets

U.S. PATENT DOCUMENTS

| | | | |
|---|---|---|---|
| 1,637,153 A | 7/1927 | Lawton | |
| 2,257,709 A | 9/1941 | Anderson | 128/260 |
| 2,835,628 A | 5/1958 | Saffir | 167/84 |
| 3,339,547 A | 9/1967 | Drabkowski | 128/260 |
| 3,527,219 A | 9/1970 | Greenberg | 128/260 |
| 3,577,640 A | 5/1971 | Lee | 32/32 |
| 3,624,909 A | 12/1971 | Greenberg | 32/40 |
| 3,688,406 A | 9/1972 | Porter et al. | 32/40 R |
| 3,955,281 A | 5/1976 | Weitzman | 32/14 B |
| 4,044,762 A | 8/1977 | Jacobs | 128/136 |
| 4,063,552 A | 12/1977 | Going et al. | 128/136 |
| 4,064,628 A | 12/1977 | Weitzman | 32/14 B |
| 4,138,814 A | 2/1979 | Weitzman | 32/14 B |
| RE33,093 E | 10/1989 | Schiraldi et al. | 424/676 |
| 4,900,721 A | 2/1990 | Bansemir | |
| 4,902,227 A | 2/1990 | Smith | 433/215 |
| 5,008,093 A | 4/1991 | Merianos | |
| 5,051,476 A | 9/1991 | Uji et al. | 525/186 |
| 5,085,585 A | 2/1992 | Zimble | 433/80 |
| 5,108,742 A | 4/1992 | Merianos | |
| 5,112,225 A | 5/1992 | Diesso | 433/48 |
| 5,183,901 A | 2/1993 | Login et al. | |
| 5,211,559 A | 5/1993 | Hart et al. | 433/80 |
| 5,310,563 A | 5/1994 | Curtis et al. | 424/616 |
| 5,326,685 A | 7/1994 | Gaglio et al. | 433/215 |
| 5,346,061 A | 9/1994 | Newman et al. | 206/221 |
| 5,356,291 A | 10/1994 | Darnell | 433/216 |
| 5,376,006 A | 12/1994 | Fischer | 433/215 |
| 5,425,953 A | 6/1995 | Sintov et al. | 424/404 |
| 5,562,449 A | 10/1996 | Jacobs et al. | 433/215 |
| 5,573,399 A | 11/1996 | McClintock, II | 433/80 |
| 5,575,654 A | 11/1996 | Fontenot | 433/215 |
| 5,611,687 A | 3/1997 | Wagner | 433/80 |
| 5,616,027 A | 4/1997 | Jacobs et al. | 433/37 |
| 5,631,000 A | 5/1997 | Pellico | 424/53 |
| 5,639,445 A | 6/1997 | Curtis et al. | 424/49 |
| 5,702,251 A | 12/1997 | McClintock, II | 433/80 |
| 5,707,235 A | 1/1998 | Knutson | 433/213 |
| 5,711,935 A | 1/1998 | Hill et al. | 424/49 |
| 5,723,143 A * | 3/1998 | Jacques et al. | 424/435 |
| 5,752,826 A | 5/1998 | Andreiko | 433/41 |
| 5,769,633 A | 6/1998 | Jacobs et al. | 433/37 |
| 5,816,802 A | 10/1998 | Montgomery | 433/80 |
| 5,846,058 A | 12/1998 | Fischer | 433/216 |
| 5,851,512 A | 12/1998 | Fischer | 424/49 |
| 5,863,202 A | 1/1999 | Fontenot et al. | 433/215 |
| 5,879,691 A | 3/1999 | Sagel et al. | 429/401 |
| 5,891,453 A | 4/1999 | Sagel et al. | 424/401 |
| 5,894,017 A | 4/1999 | Sagel et al. | 424/401 |
| 5,895,218 A | 4/1999 | Quinn et al. | 433/80 |
| 5,922,307 A | 7/1999 | Montgomery | 424/53 |
| 5,924,863 A | 7/1999 | Jacobs et al. | 433/80 |
| 5,980,249 A | 11/1999 | Fontenot | 433/80 |
| 5,985,249 A | 11/1999 | Fischer | 424/49 |
| 5,989,569 A | 11/1999 | Dirksing et al. | 424/401 |
| 6,045,811 A | 4/2000 | Dirksing et al. | 424/401 |
| 6,080,397 A | 6/2000 | Pfirrmann | |
| 6,089,869 A | 7/2000 | Schwartz | 433/215 |
| 6,096,328 A | 8/2000 | Sagel et al. | 424/401 |
| 6,106,293 A | 8/2000 | Wiesel | 433/215 |
| 6,126,443 A | 10/2000 | Burgio | 433/215 |
| 6,136,297 A | 10/2000 | Sagel et al. | 424/49 |
| 6,142,780 A | 11/2000 | Burgio | 433/80 |
| 6,155,832 A | 12/2000 | Wiesel | 433/215 |
| 6,183,251 B1 | 2/2001 | Fischer | 433/48 |
| 6,197,331 B1 | 3/2001 | Lerner et al. | 424/448 |
| 6,247,930 B1 | 6/2001 | Chiang et al. | 433/80 |
| 6,274,122 B1 | 8/2001 | McLaughlin | 424/53 |
| 6,277,458 B1 | 8/2001 | Dirksing et al. | 424/42.3 |
| 6,280,196 B1 | 8/2001 | Berghash | 433/215 |
| 6,287,120 B1 | 9/2001 | Wiesel | 433/215 |
| 6,309,625 B1 | 10/2001 | Jensen et al. | 424/49 |
| 6,312,671 B1 | 11/2001 | Jensen et al. | 424/53 |
| 6,322,360 B1 | 11/2001 | Burgio | 433/80 |
| 6,331,292 B1 | 12/2001 | Montgomery | 424/53 |
| 6,343,932 B1 | 2/2002 | Wiesel | 433/215 |
| 6,364,665 B1 | 4/2002 | Trettemerp | 433/215 |
| 6,379,147 B1 | 4/2002 | Georgakis et al. | 433/37 |
| 6,419,903 B1 | 7/2002 | Xu et al. | 424/49 |
| 6,419,906 B1 | 7/2002 | Xu et al. | 424/53 |
| 6,435,873 B1 | 8/2002 | Burgio | 433/80 |
| 6,440,396 B1 | 8/2002 | McLaughlin | 424/49 |
| 6,458,380 B1 | 10/2002 | Leaderman | 424/443 |
| 6,461,158 B1 | 10/2002 | Sagel et al. | 433/30 |
| 6,488,914 B1 | 12/2002 | Montgomery | 424/53 |
| 6,497,575 B1 | 12/2002 | Zavitsanos et al. | 433/215 |
| 6,500,408 B1 | 12/2002 | Chen | 424/53 |
| 6,503,486 B1 | 1/2003 | Xu et al. | 424/53 |
| 6,506,053 B1 | 1/2003 | Wiesel | 433/215 |
| 6,514,483 B1 | 2/2003 | Xu et al. | 424/53 |
| 6,514,484 B1 | 2/2003 | Rajaiah et al. | 424/53 |
| 6,551,579 B1 | 4/2003 | Sagel et al. | 424/53 |
| 6,649,147 B1 | 11/2003 | Ye et al. | |
| 6,682,721 B1 | 1/2004 | Kim et al. | |
| 6,689,344 B1 | 2/2004 | Chang et al. | |
| 6,730,316 B1 | 5/2004 | Chen | |
| 2001/0046654 A1 | 11/2001 | Zavitsanos et al. | 433/32 |
| 2002/0006387 A1 | 1/2002 | Sagel et al. | 424/53 |
| 2002/0006388 A1 | 1/2002 | Sagel et al. | 424/53 |
| 2002/0012685 A1 | 1/2002 | Sagel et al. | 424/401 |
| 2002/0018754 A1 | 2/2002 | Sagel et al. | 424/49 |
| 2002/0081555 A1 | 6/2002 | Wiesel | 433/215 |
| 2002/0164292 A1 | 11/2002 | Peterson et al. | 424/53 |
| 2002/0182154 A1 | 12/2002 | McLaughlin | 424/53 |
| 2002/0187111 A1 | 12/2002 | Xu et al. | 424/53 |
| 2002/0187112 A1 | 12/2002 | Xu et al. | 424/53 |
| 2003/0003421 A1 | 1/2003 | Besenheider et al. | 433/215 |
| 2003/0012747 A1 | 1/2003 | Peterson | 424/53 |
| 2003/0036037 A1 | 2/2003 | Zavitsanos et al. | 433/215 |
| 2003/0044631 A1 | 3/2003 | Sagal et al. | 428/548 |
| 2003/0068284 A1 | 4/2003 | Sagel et al. | 424/53 |
| 2003/0068601 A1 | 4/2003 | Zavitsanos et al. | 433/215 |
| 2003/0082114 A1 | 5/2003 | Kim et al. | 424/53 |
| 2003/0133884 A1 | 7/2003 | Chang et al. | 424/53 |
| 2003/0194382 A1 | 10/2003 | Chang et al. | 424/53 |
| 2003/0198606 A1 | 10/2003 | Kim et al. | 424/53 |

FOREIGN PATENT DOCUMENTS

| WO | WO 03/000216 | 1/2003 |
|---|---|---|

* cited by examiner

US 7,056,118 B2

COMPOSITIONS AND DEVICES HAVING A TRAY-LIKE CONFIGURATION FOR DELIVERING A MEDICAMENT AND METHODS OF MANUFACTURING AND USING SUCH COMPOSITIONS AND DEVICES

CROSS-REFERENCE TO RELATED APPLICATIONS

This application is a continuation-in-part of U.S. application Ser. No. 10/637,237, filed Aug. 8, 2003, which is a continuation-in-part of copending U.S. application Ser. No. 10/446,235, filed May 27, 2003 and a continuation-in-part of copending U.S. application Ser. No. 10/446,471, filed May 27, 2003. The foregoing applications are incorporated herein in their entirety.

BACKGROUND OF THE INVENTION

1. The Field of the Invention

The present invention is in the field of compositions and devices used to deliver a medicament to a person's teeth and/or gingiva. More particularly, the invention relates to medicament compositions in the shape of a dental tray, and devices that utilize such compositions, that become adhesive when moistened (e.g., by saliva in a user's mouth), as well as methods for their manufacture and use.

2. The Relevant Technology

Bacterial infections or other oral tissue irritants are a common problem for many dental patients. Such infections and/or irritants may be caused from or be associated with inflammation, bleeding, plaque accumulation, calculus (tartar) accumulation, bad breath, gingivitis, periodontitis, cavities, abscesses, canker sores, cold sores, pustulas, etc. Such bacterial infections/irritants can become so uncomfortable that it may prevent a patient from eating or drinking certain foods, socializing, or maintaining good oral hygiene practices.

To relieve and treat bacterial infections and/or oral tissue irritants, there are currently many non-permanent treatment options available. The most common options include using medicament toothpastes, varnishes, gels, and rinses. These products may include, but are not limited to, medicaments such as chlorhexidine gluconate, cetylpyridinium chloride, phenol, minocycline, tetracycline, doxycycline, penicillin, clindamycin, ciprofloxacin, metronidazole, and tricolsan.

Medicament dentifrices are a popular treatment option in treating bacterial infections and/or oral irritants. To use medicament dentifrices, it is usually recommended that the patient use the dentifrice twice daily. However, results are not immediate. It usually takes an extended period of time (about 1–4 weeks) to see any results from the medicament dentifrice. The main reason for this is that people typically only brush their teeth for about 60 seconds or less, which translates into extremely limited contact time between the medicament and the person's teeth and/or gingiva.

Another common treatment option involves the use of medicament rinses. To use medicament rinses, a patient usually "swishes" the rinse within their mouth several times per day. However, rinses only temporarily remain on oral surfaces and are only capable of providing momentary exposure to the medicament due to common movements of the patient's mouth, jaw, and tongue.

Medicament gels may also be used to treat bacterial infections and/or oral irritants and can be applied using custom-fitted trays. The process of making a custom-fitted tray generally involves: (1) making an alginate impression of the patient's teeth; (2) making a stone cast or model of the impression; (3) vacuum forming a dental tray from the model, usually from a heated sheet of thin ethyl vinyl acetate (EVA) material, and (4) trimming to allow for the desired amount of gingival coverage. This method results in a tray that is soft and flexible, that is customized to very accurately fit over the patient's teeth and gingiva, and that is therefore very comfortable to wear. In sum, the process for making a customized tray is time consuming, often taking days or weeks before the customized tray is available to the patient, and the resulting tray can be expensive.

Because of the time and cost associated with customized trays, less time consuming and costly alternatives have been developed. One alternative to customized dental trays is non-customized trays that approximate the shapes and sizes of a variety of users' dental arches. While non-customized dental trays can be used without the need for a professional customization procedure by a dentist, such trays tend to be more bulky and less comfortable than custom-fitted trays. Dental trays that can be self-customized (e.g., so-called "boil and bite" trays) are somewhat more comfortable and better-fitting compared to non-custom trays but less comfortable than trays that are customized by a dentist.

An alternative to the use of dental trays involves placing a flexible dental treatment strip over a user's teeth and/or gingival surfaces, typically for bleaching. Dental strips typically comprise a flexible plastic strip coated with a moist dental gel on the side of the strip facing the user's teeth and gingiva. To install the strip, a portion of the strip is first placed over the front surfaces of the user's teeth and/or gingiva, followed by folding the remainder of the strip around the occlusal edges of the teeth and back against a portion of the lingual surfaces of the teeth and gingiva. Like paint-on bleaching compositions, the use of dental strips does not require the user to use a customized or non-customized tray. An advantage of dental strips over paint-on compositions is that strips include a barrier that, at least in theory, protects the moist gel composition from diffusing into the user's mouth.

In reality, because of the generally poor adhesion of dental strips to the user's teeth and gingiva, coupled with their generally flimsy nature, it is often difficult for the user to maintain the strips in their proper position. Dental strips are prone to slip off the teeth and/or gingiva through even minimal movement of the user's mouth, jaw or tongue. Indeed, it is recommended that the user not eat, drink, smoke or sleep while wearing dental strips.

Even if a user successfully maintains the strip in its proper position during the entire treatment time, the flowable gel composition can diffuse into the person's saliva, potentially causing a poor taste in the user's mouth and possibly discomfort to soft oral and throat tissues. The tendency of the gel to diffuse into the user's mouth can be accelerated through even minimal shifts of the dental strip over the user's teeth/gingiva, with each shift potentially exposing a new portion of the gel that remains adhered to the newly exposed surface of the user's teeth/gingiva. In some cases, the dental strip can become so dislodged or mangled that it must be removed by the user and replaced with a fresh strip to complete the recommended treatment time. This multiplies the cost and hassle of the dental strip method.

In practical terms, the use of dental strips can greatly inhibit even the simplest of activities that involve movement of the user's mouth or tongue, such as talking, coughing, yawning, smiling, making other facial expressions, or even swallowing (which normally occurs subconsciously throughout the day). Indeed, the time when a person's mouth and tongue are prone to move the least is at night while the person is sleeping. Unfortunately, it is recommended that dental strips not be used while sleeping, presumably to prevent accidental choking on an inadvertently dislodged strip. This only confirms the tendency of conventional dental strips to easily dislodge from a user's teeth and/or gingiva.

In view of the foregoing, there is an ongoing need for improved medicament compositions, apparatus and methods that are simple and easy to use, that more reliably remain in position over a user's teeth and/or gingiva, and that result in less diffusion of medicament compositions into a user's oral cavity. Such improvements would be expected to improve or encourage compliance by the user.

BRIEF SUMMARY OF THE PREFERRED EMBODIMENTS

The present invention generally relates to shaped medicament compositions and devices used to deliver a medicament to a person's teeth and/or gingiva, as well as methods for manufacturing and using such compositions and devices. Briefly summarized, the inventive medicament compositions are in a substantially solid form and shaped like a dental tray or in tray-like configuration. The substantially solid medicament compositions become more adhesive to teeth and/or gingiva when moistened (e.g., by saliva or water). When placed over a person's teeth and/or gingiva, the medicament composition reliably adheres to the teeth and/or gingiva, maintaining contact between the teeth and/or gingiva to be treated and the medicament within the medicament composition.

In one embodiment, the shaped medicament composition is used in combination with a barrier layer that protects the medicament composition from ambient saliva or moisture found within the person's mouth. To the extent that a barrier layer is subsequently applied or attached to a shaped medicament composition, the shaped medicament composition may be considered to be an intermediate to a finished medicament treatment device comprising the medicament composition and the barrier layer.

The optional barrier layer advantageously comprises a thin, flexible membrane formed from a moisture-resistant polymer material. Nevertheless, it is within the scope of the invention to provide barrier layers having any desired thickness or rigidity. In a preferred embodiment, the barrier layer comprises a thin layer of a polyolefin, polyester or similar moisture-resistant material. The barrier layer may comprise a conventional dental tray, examples of which include both customized and non-custom dental trays. The barrier layer may be as simple as a layer of a moisture resistant barrier forming material that is sprayed or painted on, applied by dipping, or otherwise applied to an existing medicament treatment layer comprising a substantially solid medicament composition (e.g., one that is in the form of a dental tray or that otherwise has a desired shape).

The medicament composition is substantially solid and coherent, as opposed to a liquid, gel, paste, or dry particulate or powdery medicament composition. As such, the medicament composition comprises one or more coherent regions or masses of a medicament composition that do not readily run or flow. Providing a substantially solid and coherent medicament composition better adheres to a person's teeth and/or gingiva and does not readily diffuse into the surrounding oral cavity on its own, absent becoming diluted by saliva or moisture in a person's mouth. This helps maintain the medicament composition between the optional barrier layer and the teeth and/or gingiva being treated and helps prevent diffusion into the surrounding oral cavity. This, in turn, promotes better medication of the targeted oral tissue, patient compliance, and reduces the tendency of the user to taste the medicament composition when in use.

The substantially solid medicament compositions according to the invention include at least one medicament and at least one tissue adhesion agent. Exemplary antimicrobial agents that can be used to treat gingivitis, periodontal disease, plaque or other oral bacterial infections or maladies include, but are not limited to, chlorhexidine gluconate, cetylpyridinium chloride, phenol, minocycline, tetracycline, doxycycline, penicillin, clindamycin, ciprofloxacin, metronidazole, and tricolsan. Exemplary remineralizing agents capable of preventing caries include, but are not limited to, sodium fluoride, sodium monofluorophosphate, stannous fluoride, and calcium phosphate. Exemplary anti-tartar agents include, but are not limited to, pyrophosphates, polypyrophosphates, polyvinyl methyl ether malic acid, sodium hexametal phosphate, alkali metal phosphates, calcium lactate, and triclosan. Exemplary anticalculus or anti-plaque agents include, but are not limited to, 8-hydroxyquinoline sulfate, dicitrate cyclic ester, and zinc citrate.

In one embodiment, the tissue adhesion agent advantageously remains substantially non-adhesive when the medicament composition is in a dry or substantially solid condition but becomes adhesive to teeth and/or gingiva when the medicament composition is moistened, e.g., with water or saliva. A non-limiting example of a suitable tissue adhesion agent is polyvinyl pyrrolidone (PVP), although it is within the scope of the invention to use other tissue adhesion agents known in the art.

The medicament composition may include other components in addition to a medicament for treating teeth or surrounding gingiva, as desired, to yield a final composition having desired properties. Examples of other components include, but are not limited to, plasticizers and humectants (e.g., glycerin, sorbitol, and polyethylene glycol), volatile solvents (e.g., water and alcohols), stabilizing agents (e.g., EDTA), neutralizing agents, thickening agents (e.g., fumed silica), bleaching agents (e.g., hydrogen peroxide), desensitizing agents (e.g., potassium nitrate) flavorants, sweeteners, and the like.

According to one embodiment, the medicament composition is made by first forming a flowable liquid or gel composition that is subsequently dried to form a substantially solid medicament layer. This may be performed by heating or otherwise causing one or more volatile solvents to be driven off by evaporation, thus leaving behind a substantially solid medicament composition. The drying process may be performed before or after the medicament composition is placed into contact with the barrier layer.

According to one embodiment, shaped medicament compositions according to the invention can be made by spreading a flowable medicament composition onto the surface of a large or continuous polymeric sheet. The polymeric sheet and medicament composition are then heated, such as in a forced air oven, to drive off a substantial portion of the water or other solvent that was used to form the flowable medicament composition in order to yield a substantially solid layer of medicament composition. Thereafter, individual tray-like treatment devices can be molded or stamped from the large or continuous polymeric sheet coated with the substantially solid layer of medicament composition and then separated as individual treatment devices suitable for placement over a person's teeth and/or gingiva. Such treatment devices include a medicament layer comprising a shaped medicament composition according to the invention. Alternatively, the solid sheet of medicament composition can be separated from the polymer sheet and molded, stamped or otherwise formed into a desired shape.

Alternatively, a flowable or substantially solid medicament composition can be molded or shaped into a desired tray-like configuration comprising the medicament layer. Alternatively, the flowable composition can be cast onto a forming surface and dried to form a substantially solid sheet of medicament composition that is thereafter molded, stamped or otherwise formed into a desired shape. Thereafter, a barrier layer can be attached or applied to an outer surface of the medicament layer. In yet another embodiment, a dental tray can be coated with a flowable medicament composition, such as by painting or spreading, and then heated or allowed to dry at room temperature so that the medicament composition becomes substantially solid.

The size and shape of medicament compositions and treatment devices incorporating such compositions according to the invention can be tailored to more readily fit a person's upper or lower dental arch. They may also be tailored to fit persons having differently sized or shaped dental arches. The medicament compositions and devices are advantageously designed so as to substantially cover the front and lingual surfaces of the teeth and, optionally, the surrounding gingiva to be medicated. Treating both surfaces provides more complete medication of the whole tooth/gingiva, not just one side. The medicament treatment devices may advantageously be flexible and adhesive so as to readily conform to a wide variety of differently-sized teeth, gingiva, and dental arches.

The medicament compositions according to the invention are preferably in the shape of a dental tray having a front side wall, a rear side wall, and a trough between the front and rear side walls. Having the shape of a dental tray facilitates placement of the medicament composition or treatment device over a person's teeth and/or gingiva by minimizing the amount of manipulation that is necessary to obtain a good fit between the composition or device and the person's teeth and/or gingiva. Medicament treatment devices that are in the shape of a dental tray and that have a substantially solid medicament layer that becomes more adhesive when moistened with water or saliva are easier to install over a person's teeth and/or gingiva than flat dental strips. In addition, the inventive medicament devices are designed to more reliably remain in place over the person's teeth and/or gingiva compared to conventional dental treatment strips. The result is more effective medication of a person's teeth and/or gingival and better patient compliance.

According to one embodiment, the medicament composition or device has a horseshoe shape and a U-shaped trough like a conventional tray. In another embodiment, the medicament composition or device has an L-shaped profile or "trough". It will be appreciated, however, that medicament compositions or devices according to the invention can have any longitudinal profile or shape (e.g., they can be straight or have any desired degree of longitudinal curvature from one end of the device to the other). The trough may have any desired cross-sectional shape (e.g., the trough can be V-shaped, trapezoidal, rectangular, or other geometric shape).

To facilitate the ability of a treatment composition or device to conform to the various shapes and sizes among dental arches, the dental treatment composition or device may include mechanical features such as a notch within the front side wall, preferably within an edge near the center of the front side wall, and/or a notch within the rear side wall, preferably within an edge near the center of the rear side wall. Notches allow the tray-like medicament composition or device to more easily conform to differently-sized dental arches. In this way, the medicament composition or device can be designed so as to be "one-size fits all."

The medicament compositions, as well as medicament devices incorporating such compositions, can be designed to be worn for any desired time period. Increasing the concentration of medicament generally reduces the time it takes to carry out a desired medication procedure. Nevertheless, due to the extremely comfortable fit and reliable adhesion between the inventive medicament devices and the person's teeth and/or gingiva, it is possible to wear such devices for extended periods of time in order to ensure even and thorough delivery of the medicament. Medicament compositions according to the invention can be designed to be worn while, e.g., talking, sleeping, eating, drinking, smiling, frowning, grimacing, yawning, coughing, smoking, or making virtually any facial expression or mouth contortion. This greatly decreases their intrusiveness into everyday activities compared to conventional dental treatment strips, which do not reliably adhere to teeth and/or gingiva, or intrusive treatment devices such as large, bulky dental appliances.

The medicament compositions, as well as devices incorporating such compositions can be designed to be worn for as little as a few minutes or as long as several hours. By way of example and not limitation, such compositions usually require less time to be effective and can generally be worn for short durations (10–30 minutes), intermediate durations (30 minutes–2 hours), or long durations (2–12 hours) if needed. Treatment sessions may also be repeated as many times as are needed to obtain the desired degree of medication of teeth and/or gingiva.

For convenience of use, multiple medicament compositions, as well as devices incorporating such compositions, may be packaged together and sold as a kit, either alone or in combination with other oral treatments (e.g., dental bleaching compositions, desensitizing compositions, or treatment devices incorporating such compositions). In one embodiment, the number of medicament compositions or devices provided with each kit can equal the number of sessions that represent a prescribed treatment regimen. To efficiently utilize the space within a kit package, multiple medicament compositions or devices can be stacked and inserted together. The medicament compositions or devices can be sealed collectively or individually as desired. They may contain a removable protective layer on their interior surfaces to protect the medicament layer from contamination or moisture. It is within the scope of the invention to provide barrier layers and medicament compositions that are initially separate and that are brought together by the end user. The medicament composition may be a dry or substantially solid insert or it may be a liquid or gel that is applied to the barrier and allowed to dry prior to placement of the finished dental treatment device over the person's teeth and/or gingiva.

These and other advantages and features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by references to specific embodiments thereof, which are illustrated in the appended drawings. It is appreciated that these drawings depict only typical embodiments of the invention and are therefore not to be considered limiting of its scope. The invention will be described and explained with additional specificity and detail through the use of the accompanying drawings in which.

DETAILED DESCRIPTION OF THE PREFERRED EMBODIMENTS

I. Introduction and Definitions

Figure 1:
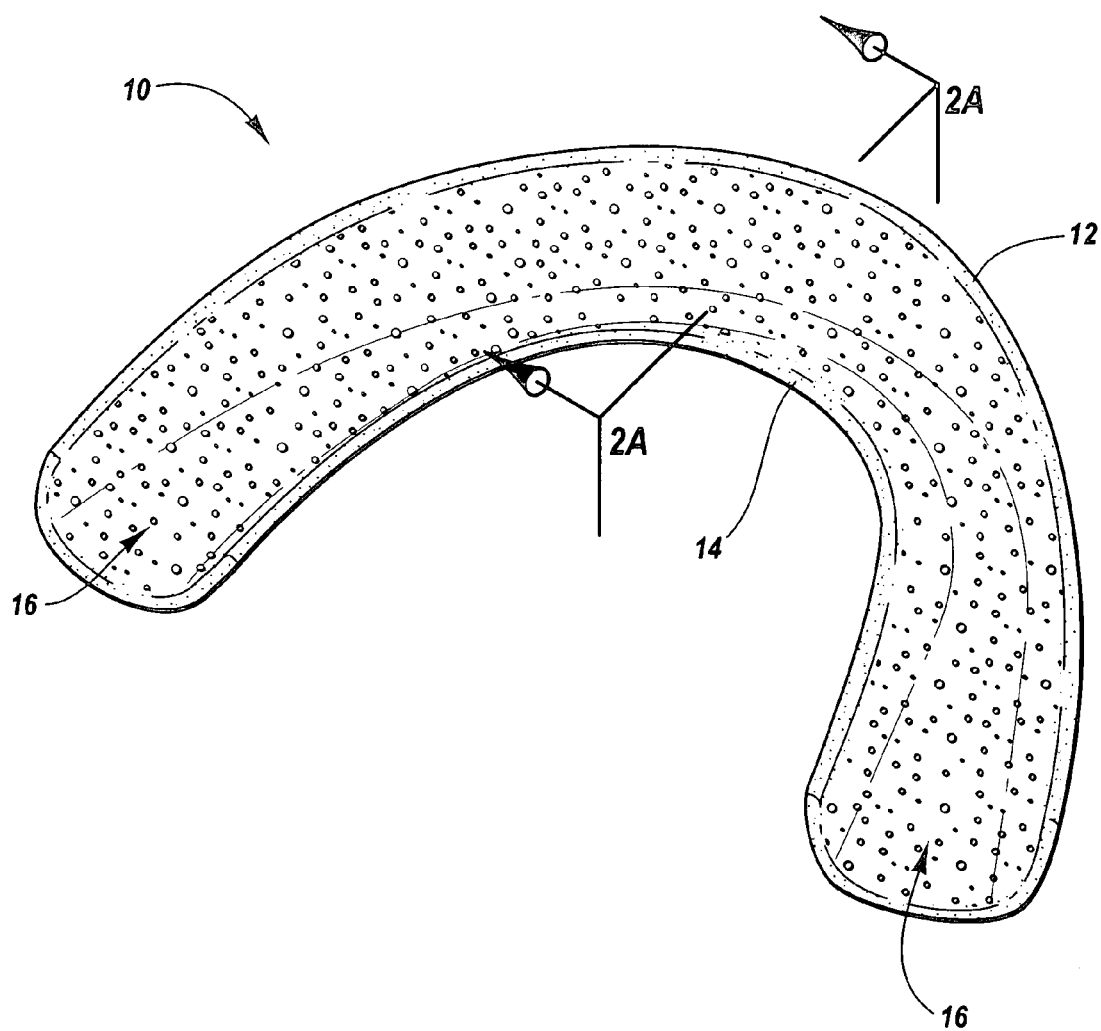
FIG. 1 is a perspective view of an exemplary treatment device according to the invention in the shape of a dental tray comprising a barrier layer and a substantially solid medicament composition.

The present invention generally relates to improved medicament compositions and treatment devices that include such compositions for use in providing one or more medicaments to a person's teeth and/or gingiva, as well as methods for manufacturing and using such compositions and devices. The shaped medicament compositions are in a substantially solid form that becomes more adhesive to teeth and/or gingiva when moistened with water or saliva. When placed over a person's teeth and/or gingiva, the medicament composition reliably adheres to the teeth and/or gingiva, maintaining contact between the teeth and/or gingiva to be treated and a medicament within the medicament composition. A barrier layer may be provided that protects the medicament composition from diffusing away from the person's teeth and/or gingiva as a result of ambient saliva or moisture found within the person's mouth.

The shaped medicament compositions are more adhesive to teeth and/or gingiva than conventional dental treatment strips. Treatment devices incorporating such compositions are also less intrusive than bulky, over-the-counter, non-custom or boil and bite dental trays. In some ways they are as reliable as, or even more reliable than, custom-fitted dental trays in maintaining the medicament composition against a person's teeth and/or gingiva. In some cases, they are also as comfortable, or even more comfortable, than custom-fitted trays.

The term "barrier layer", as used herein, refers to one or more layers of a moisture-resistant material that protects the medicament layer from ambient moisture and saliva found within a person's mouth when the medicament composition is placed over the person's teeth and/or gingiva. The barrier layer may also serve to protect the medicament composition from moisture or other contaminants during storage and prior to use. The barrier layer may be in any desired form including, but not limited to, a sheet laminated to a surface of the medicament layer, a coating applied to a pre-formed medicament layer, or a dental treatment tray.

The term "shaped medicament composition", as used herein, refers to a medicament composition that has been formulated or processed so as to be substantially solid, coherent, and non-flowable. The term "medicament layer", as used herein, refers to one or more layers of a medicament composition that has been formulated or processed so as to be substantially solid, coherent, and non-flowable. The medicament layer may comprise a single continuous region or layer adjacent to the barrier layer, or it may comprise a plurality of discontinuous regions or layers spaced-apart by random or predetermined intervals.

The term "substantially solid", as used herein, refers to a medicament composition or layer that is in a solid or semi-solid condition so that it can be handled and placed against a person's teeth much like a dental tray. In one aspect, a "substantially solid" medicament composition or layer can be characterized as a continuous or cohesive mass that does not readily flow or separate when subjected to gravitational forces and which cannot be readily expressed through a syringe outlet or other similarly-sized opening or orifice. Thus, the term "substantially solid" excludes runny medicament liquids, viscous medicament liquids, and even thick medicament gels that are able to flow when subjected to gravity and/or which can be readily expressed through a syringe outlet or other similarly-sized opening or orifice. The term "substantially solid", when used in the context of a medicament composition or layer, excludes dry particulate compositions or powders because dry particulates and powders readily flow when subjected to gravity and/or are readily separated (i.e., the particles as a whole have little or no internal cohesion). Moreover, powders or particulates, when viewed as a whole, are not "shaped", coherent, or solid. One characteristic of "substantially solid" medicament compositions or layers according to the invention is that they become more adhesive when an exposed surface thereof is moistened with, e.g., saliva or water. When moistened, the surface of the medicament composition or layer turns into a sticky material that is able to more strongly adhere to teeth and/or gingiva compared to a substantially solid medicament composition or layer that has not been moistened. The medicament composition at the surface may become a viscous liquid, paste or gel, at least temporarily, depending on the amount of moisture that is applied to the surface of the "substantially solid" medicament composition or layer. Nevertheless, the consistency of the moistened surface can remain "substantially solid" depending on the degree of initial moistening, or it can stiffen and even revert back to being "substantially solid" as the initial quantity of surface moisture diffuses into a remaining portion of the "substantially solid" medicament composition or layer over time (e.g., during a medicament procedure in which the medicament layer or composition is protected from saliva and ambient moisture in a person's mouth by a water-proof barrier layer).

The term "dental tray", as used herein, refers to any article of manufacture or device having a tray-like shape so as to facilitate placement of the device over at least a portion of a person's dental arch. A "dental tray" or "tray-like" device includes a front side wall configured to engage front surfaces of a person's teeth when in use, a rear side wall extending laterally from the front side wall, either abruptly by one or more distinct angles or non-abruptly by a curved transition, configured to engage lingual surfaces of the person's teeth, and a trough between said front and rear side walls. A "dental tray" may be configured so that a portion of the front side wall, rear side wall, or a transition portion thereof engages the incisal or occlusal edges of the person's teeth when in use. The dental tray may be curved or straight in the longitudinal dimension.

The term "trough", as used herein, refers to the region that is at least partially bounded by the front side wall, the rear side wall, and a plane or imaginary curved dome extending from an upper edge of the front side wall and an upper edge of the rear side wall. Thus, a "trough" can theoretically exist whenever the front and rear side walls have a space there between and are laterally offset by an angle of less than 180°. In practice, the front and rear side walls will be offset by an angle that is preferably less than about 150°, more preferably less than about 120°, and most preferably less than about 90°.

In the case of a trough having a U-shaped or rectangular cross section, at least a portion of the front and rear side walls may be substantially parallel (i.e., be offset by an angle of approximately 0°). In the case of a trough having a V-shaped or trapezoidal cross section, at least a portion of the front and rear side walls may be offset by an acute angle (i.e., by an angle between 0–90°). In the case of a trough having an L-shaped cross section, at least a portion of the front and rear side walls will be offset by an angle centered around approximately 90° (e.g., by an angle in a range of about 70° to about 110°). Thus, a trough having an L-shaped cross section can be a subset or slight variation of a trough having a V-shaped cross section.

The terms "longitudinal", "longitudinal dimension" and "longitudinal profile", as used herein when used to refer to a dental tray or dental treatment device, shall refer to the lengthwise dimension of the tray or device. The tray or device may be straight in the "longitudinal dimension" or it may be horseshoe-shaped or otherwise "longitudinally curved" in the longitudinal dimension so as to approximate the curvature of a person's dental arch, or at least facilitate placement of the tray or device over the dental arch.

The term "molecular weight", as used herein, refers to number average molecular expressed in Daltons unless otherwise specified.

II. Medicament Compositions and Devices

The shaped medicament compositions can exist alone or in combination with a barrier layer as part of a treatment device. Such treatment devices typically include a shaped medicament composition or layer that becomes more adhesive to teeth and/or gingiva when moistened by, e.g., saliva or water, and a moisture-resistant barrier layer that protects the medicament layer from ambient moisture within a person's mouth during use. Following are preferred examples of materials and characteristics of barrier layers and medicament compositions or layers according to the invention.

A. Barrier Layers

According to one embodiment of the invention, the barrier layer comprises a thin, flexible membrane formed from a moisture-resistant polymer material. In a preferred embodiment, the barrier layer comprises a thin, flexible layer of a polyolefin or similarly moisture-resistant material, such as wax, metal foil, paraffin, ethylene-vinyl acetate copolymer (EVA), ethylene-vinyl alcohol copolymer (EVAL), polycaprolactone (PCL), polyvinyl chloride (PVC), polyesters, polycarbonates, polyamides, polyurethanes or polyesteramides. Such materials may be provided in the form of large, flat, flexible sheets to which the medicament composition or layer is applied. Alternatively, such sheets may be applied or attached to an existing medicament layer comprising a substantially solid medicament composition.

Notwithstanding the foregoing, it is within the scope of the invention to provide barrier layers having any desired material, thickness or rigidity so long as the barrier layer provides at least some moisture protection relative to the shaped medicament layer. The barrier layer may comprise a conventional dental tray, examples of which include both customized and non-custom dental trays. The barrier layer may be as simple as a layer of a moisture resistant material that is sprayed or painted on, applied by dipping, or otherwise applied to an existing medicament composition (e.g., one that is in the form of a dental tray or that otherwise has a desired shape).

Examples of suitable polyolefins for use in making the barrier layer include, but are not limited to, polyethylene (PE), high density polyethylene (HDPE), low density polyethylene (LDPE), ultra low density polyethylene (ULDPE), polypropylene, and polytetrafluoroethylene (PTFE) (e.g., TEFLON). An example of a suitable polyester for use in making the barrier layer includes, but is not limited to, polyethylene terephthalate (PET), an example of which is MYLAR, sold by DuPont. An example of a suitable polyurethane barrier material is a polyurethane film manufactured by ArgoTech, which is located in Greenfield, Mass. Plasticizers, flow additives, and fillers known in the art can be used as desired to modify the properties of any of the foregoing polymers used to form the barrier layer.

As will be discussed below, some medicament compositions will be more adhesive to polymer materials comprising the barrier layer than others, often depending on the adhesion agent that is used. It has been found that, as between polyethylene, paraffin and polyethylene terephthalate, substantially solid medicament compositions tend to adhere more strongly to polyethylene terephthalate, particularly MYLAR.

It is also within the scope of the invention to utilize barrier layers that are formed onto a surface of a previously formed medicament composition, such by adhering a sheet or tray-like barrier layer to the medicament composition, which may then be thought of as a "medicament layer". Alternatively, the barrier layer may itself be initially flowable and later hardened, such as a lacquer that contains a barrier material (e.g., a cellulosic ether, cellulose acetate, wax, plastic, polyvinyl acetate, polyvinyl alcohol, or shellac) dissolved in one or more solvents that are later removed; a chemical or light-cure material (e.g., a methacrylate or acrylate resin); or a thermoplastic melt (e.g., any thermoplastic resin). Examples of useful cellulosic ethers that can be used to form a barrier layer include, but are not limited to, ethyl cellulose, propyl cellulose, isopropyl cellulose, butyl cellulose, t-butyl cellulose, and the like.

B. Substantially Solid Medicament Compositions and Layers

The substantially solid medicament compositions according to the invention can be in the shape of a dental tray, with or without a barrier layer. Where a barrier layer is present, the solid medicament composition may be thought of as a medicament layer. Prior to being moistened in preparation for or during use, medicament compositions or layers according to the invention preferably comprise a substantially solid and coherent medicament composition, as opposed to a liquid, a flowable gel, or a dry powder or particulate medicament composition. In the case of a medicament device, the medicament layer may comprise a single coherent mass or region, or it may comprise a plurality of coherent masses or regions of a substantially solid medicament composition adhered to the barrier layer. Providing a substantially solid and coherent medicament layer better maintains the medicament composition between the barrier layer and the teeth and/or gingiva being medicated instead of diffusing into the surrounding oral cavity, as compared to conventional medicament gels that are loaded into customized or non-customized dental trays. This, in turn, promotes better delivery of the medicament and patient compliance.

Substantially solid medicament compositions and layers according to the invention include at least one medicament and at least one tissue adhesion agent. In a preferred embodiment, the medicament is dispersed within a substantially solid matrix comprising the tissue adhesion agent. The medicament compositions may include other active agents, such as dental bleaching agents and/or dental desensitizing agents. Following are preferred medicament, tissue adhesion agents, bleaching agents, and desensitizing agents.

1. Medicaments

The term "medicament" broadly relates to any active ingredient that is able to provide a desired medicating or treatment action to the person's teeth and/or surrounding gingival tissue. Examples of useful medicaments include, but are not limited to, anti-bacterial agents used to treat, e.g., gingivitis, periodontal disease, plaque, or other oral bacterial infections or maladies; remineralizing agents capable of strengthening tooth enamel so as to prevent caries; anti-tartar agents that remove and/or prevent the build-up of tartar on a person's teeth; and anti-calculus or anti-plaque agents.

Exemplary antimicrobial agents include, but are not limited to chlorhexidine gluconate, cetylpyridinium chloride, phenol, minocycline, tetracycline, doxycycline, penicillin, clindamycin, ciprofloxacin, metronidazole, and tricolsan. A common antimicrobial agent that has been found to be safe for oral use is chlorhexidine gluconate.

Exemplary remineralizing agents capable of preventing caries include, but are not limited to, sodium fluoride, sodium monofluorophosphate, stannous fluoride, other fluoride salts, and calcium phosphate. Exemplary anti-tartar agents include, but are not limited to, pyrophosphates, polypyrophosphates, polyvinyl methyl ether malic acid, sodium hexametal phosphate, alkali metal phosphates, calcium lactate, and triclosan. Exemplary anticalculus or anti-plaque agents include, but are not limited to, 8-hydroxyquinoline sulfate, dicitrate cyclic ester, and zinc citrate.

Medicaments within the substantially solid medicament compositions according to the invention can have any desired concentration, e.g., between 0.01–75% by weight of the substantially solid medicament composition. The concentration of the medicament can be adjusted depending on the intended treatment time for a given treatment or procedure. In general, the shorter the treatment time, the more medicament may be added to accelerate the medicating affect so as to achieve a desired result within a shorter time period.

For treating periodontal disease, chlorhexidine gluconate is the preferred medicament and is preferably included in an amount in a range of about 0.01 to about 50% by weight of the substantially solid medicament composition, more preferably in a range of about 0.05% to about 25% by weight of the substantially solid medicament composition, and most preferably in a range of about 0.1% to about 10% by weight of the substantially solid medicament composition. Other anti-bacterial agents or medicaments may be included in the same concentration ranges.

2. Tissue Adhesion Agents

The tissue adhesion agent may comprise any known tackifying agent that is substantially non-adhesive, or less adhesive, when the medicament composition is substantially solid but which becomes more adhesive to teeth and/or gingiva when the medicament composition is moistened with, e.g., water or saliva. A presently preferred tissue adhesion agent is polyvinyl pyrrolidone (PVP). PVP polymers have been found to provide excellent adhesion to polymer barrier layers made from PE, PET and paraffin, to be substantially non-adhesive when the medicament composition is dry to the touch, and to have superior adhesion to teeth and/or gingiva when a surface of a substantially solid medicament composition is moistened with saliva or water.

Non-limiting examples of polyvinyl pyrrolidone polymers that may be useful in formulating medicament compositions and layers according to the invention include Kollidon 30, a polyvinyl pyrrolidone polymer sold by BASF having a molecular weight of 50,000, Kollidon VA 60, a polyvinyl pyrrolidone polymer having a molecular weight of 60,000, and Kollidon 90 F, a polyvinyl pyrrolidone polymer having a molecular weight of 1.3 million. Because PVP polymers having widely varying molecular weights have been found to provide similar adhesion and wetting properties, it is believed that PVP polymers of any molecular weight, at least those having a molecular weight between 50,000 and 1.3 million, will be useful in formulating substantially solid medicament compositions or layers according to the invention.

Other tissue adhesion agents that may be used in addition to, or instead of, PVP within the scope of the invention include, but are not limited to, carboxypolymethylene (e.g., CARBOPOL, sold by Novean, Inc.), polyethylene oxide (e.g., POLYOX, made by Union Carbide), polyacrylic acid polymers or copolymers (e.g., PEMULEN, sold by Novean, Inc.), polyacrylates, polyacrylamides, copolymers of polyacrylic acid and polyacrylamide, PVP-vinyl acetate copolymers, carboxymethylcellulose, carboxypropylcellulose, polysaccharide gums, proteins, and the like.

Although polyethylene oxide polymers comprises a less preferred tissue adhesion agent, it has been found that a polyethylene oxide polymer having a molecular weight of 1 million provides better adhesion to barrier layers such as MYLAR than a polyethylene oxide polymer having a molecular weight of 100,000.

The one or more tissue adhesion agents are preferably included in an amount in a range of about 10% to about 90% by weight of the substantially solid medicament composition (exclusive of any bound water or other solvent), more preferably in a range of about 20% to about 80% by weight of the substantially solid medicament composition, and most preferably in a range of about 40% to about 75% by weight of the substantially solid medicament composition.

3. Other Components

The medicament compositions and layers may include other components as desired to yield a final composition or layer having desired properties. Examples of other components include, but are not limited to, plasticizers and humectants (e.g., glycerin, sorbitol, and polyethylene glycol), volatile solvents (e.g., water and alcohols, such as ethanol), stabilizing agents (e.g., EDTA), neutralizing agents (e.g., sodium hydroxide), thickening agents (e.g., fumed silica), bleaching agents (e.g. carbamide peroxide and sodium perborate), desensitizing agents (e.g., potassium nitrate), flavorants, sweeteners, and the like.

When water is used as a solvent when manufacturing medicament compositions or layers according to the invention and then driven off by evaporation to yield a substantially solid medicament composition, it is postulated that a significant amount of water remains bound or associated with the hydrophilic components within the medicament composition, including the tooth adhesion agent and any polyols added as humectants. Although the amount of residual water has not yet been determined, it is believed that approximately 10% of the water added initially remains after the initially flowable medicament composition is dried sufficiently to yield a substantially solid medicament composition.

Optional bleaching agents include, but are not limited to hydrogen peroxide, metal percarbonates, complexed hydrogen peroxides (e.g., carbamide peroxide or sodium perborate), chlorites, and hypochlorites, peroxy acids, and peroxy acid salts. When included, dental bleaching agents are preferably included in an amount in a range of about 5% to about 80% by weight of the medicament composition or layer, more preferably in a range of about 10% to about 60% by weight of the medicament composition or layer, and most preferably in a range of about 20% to about 50% by weight of the medicament composition or layer.

Optional desensitizing agents include, but are not limited to potassium nitrate, other potassium salts, citric acid, citrates, strontium chloride, stannous fluoride, and sodium fluoride. When included, dental desensitizing agents are preferably included in an amount in a range of about 0.01% to about 50% weight of the medicament composition or layer, more preferably in a rage of about 0.05% to about 25% by weight of the medicament compositions or layer, and most preferably in a range of about 0.1% to about 10% by weight of the medicament composition or layer.

C. Characteristics of Medicament Compositions and Treatment Devices Incorporating such Compositions Medicament compositions according to the invention, as well as treatment devices incorporating such compositions, are preferably in the shape of a dental tray having a front side wall, a rear side wall, and a trough between the front and rear side walls. Having the shape of a dental tray facilitates placement of the medicament composition or treatment device over a person's teeth and/or gingiva by reducing the amount of manipulation that is necessary to obtain a good fit between the device and the person's teeth/gingiva.

Medicament compositions and treatment devices in the shape of a dental tray that comprise a substantially solid shaped medicament composition that becomes more adhesive when moistened with water or saliva are easier to install over a person's teeth and/or gingiva compared to dental treatment strips or patches, which are initially flat and which must be manipulated so as to wrap the initially flat strip or patch around the occlusal or incisal edges of the teeth in order to cover the front and lingual tooth surfaces. In addition, the inventive medicament compositions and devices are designed to more reliably adhere and remain in place over the person's teeth and/or gingiva compared to conventional dental strips, which employ a dental gel that is already flowable prior to placing the strip over a person's teeth to be treated. The result is more effective treatment of the person's teeth and/or gingiva and better patient compliance. In contrast to conventional bleaching strips, which are not recommended for use while a person eats, drinks, smokes or sleeps, medicament compositions and treatment devices according to the invention can be designed so as to be worn while talking, sleeping, eating, drinking, smiling, frowning, grimacing, yawning, coughing, smoking, or making virtually any facial expression or mouth contortion.

Figure 2A:
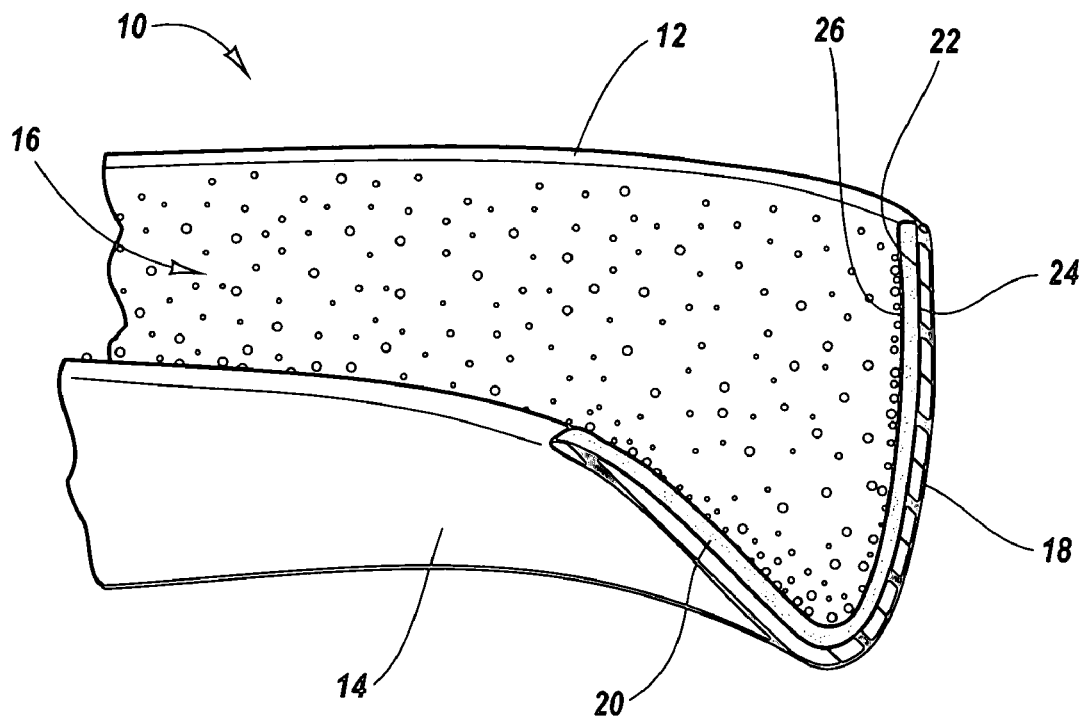
FIG. 2A is a cross-sectional view of the treatment device depicted in FIG. 1A.

According to one currently preferred embodiment, the medicament compositions and treatment devices have a horseshoe shaped longitudinal profile and a trough with a U-shaped cross section, much like a conventional dental tray. An exemplary treatment device is depicted in FIGS. 1 and 2A. FIG. 1 is a perspective view of a treatment device 10 having a front side wall 12 and a rear side wall 14 that together have a generally horseshoe shape in a longitudinal dimension and that define a trough 16 having a generally U-shaped cross section. The U-shaped cross section of the trough is seen even more clearly in FIG. 2A.

The treatment device 10 further includes a barrier layer 18, preferably comprising a moisture-resistant material, and a coherent medicament layer 20, preferably comprising a substantially solid medicament composition. As best seen in FIG. 2A, the medicament layer 20 includes an exterior surface 22 disposed adjacent to an interior surface 24 of the barrier layer 18 and an interior medicament surface 26 designed to directly contact a person's teeth and/or gingiva when the treatment device 10 is in use. An upper edge 28 of the barrier layer 18 can be designed so as to terminate at or shy of the gingival margin of a person's dental arch when in use.

Figure 2B:
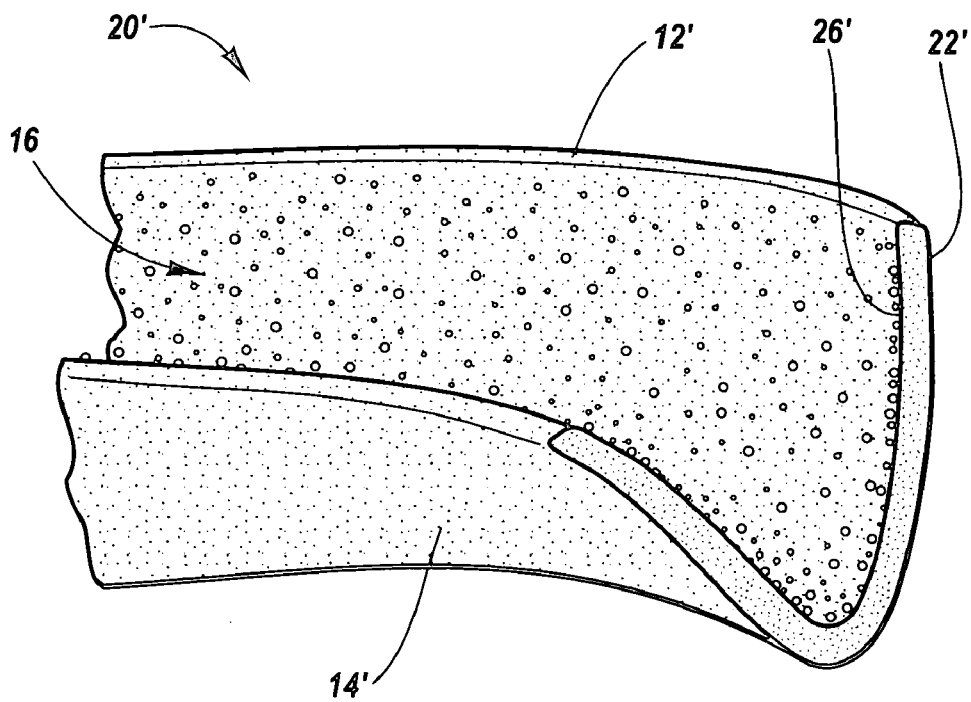
FIG. 2B is a cross-sectional view of an exemplary medicament composition according to the invention in the shape of a dental tray without a barrier layer.

FIG. 2B alternatively depicts a medicament composition 20' in the shape of a dental tray so as to have a front side wall 12' and a rear side wall 14' but with no barrier layer. The medicament composition 20' includes an interior medicament surface 26' designed to directly contact a person's teeth and/or gingiva when the composition 20' is in use and an exterior surface 22' that may optionally be coated with a water-resistant barrier layer or material if desired to protect the medicament composition 20' from saliva (see FIG. 2A). The medicament composition 20' may be sold alone or together with a barrier layer or material.

Figure 3:
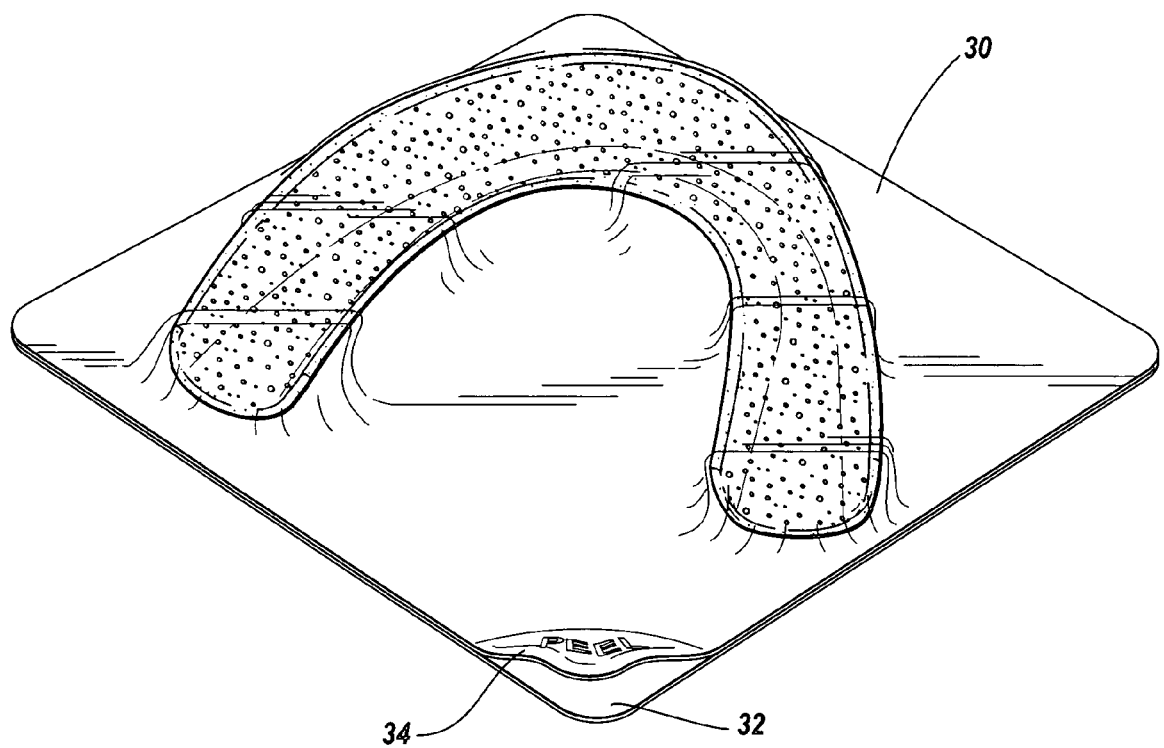
FIG. 3 illustrates a dental treatment device contained within a sealed protective package having a peelable cover.

In order to protect medicament compositions and treatment devices according to the invention from contaminants during storage and prior to use, the medicament compositions and treatment devices can be packaged within a sealed container or package. As illustrated in FIG. 3, the treatment device 10 can be sealed within a protective package 30 that includes a rigid support layer 32 and a peelable cover 34. When it is desired to use the treatment device 10, the peelable cover 34 is removed and the treatment device 10 is removed or separated from the support layer 32. In addition to, or instead of, the protective package 30, the treatment device 10 may alternatively include a removable protective layer (not shown) that is temporarily placed adjacent to the interior medicament surface 26 of the medicament layer 20. When it is desired to use the treatment device 10, the removable protective layer is removed so as to expose the interior medicament surface 20.

The protective package 30 or other protection means may also be used to protect shaped medicament compositions that do not include a barrier layer, such as the medicament composition 20' depicted in FIG. 2B.

Figure 4:
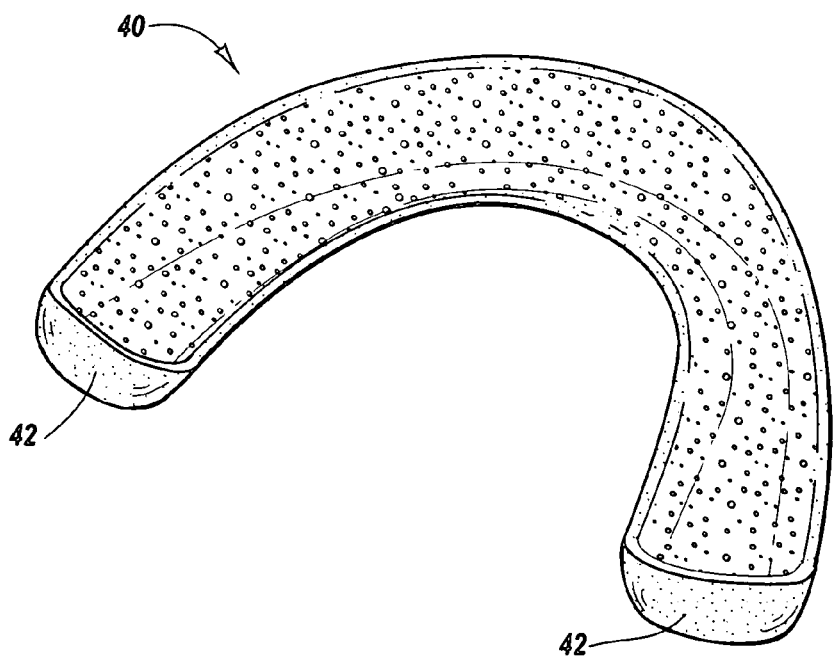
FIG. 4 is a perspective view of an exemplary medicament composition or treatment device that is similar to the treatment device depicted in FIG. 1, or the medicament composition of FIG. 2B, but that further includes a terminal side wall on each longitudinal end.

FIG. 4 illustrates a medicament composition or treatment device 40 that is a variation of the U-shaped treatment device 10 of FIGS. 1 and 2A or the medicament composition 20' shown in FIG. 2B. The main difference is that each longitudinal end 42 of the medicament composition or treatment device 40 is raised so as to at least partially enclose the last tooth on each side of a person's dental arch when the medicament composition or treatment device 40 is in use.

Figure 5:
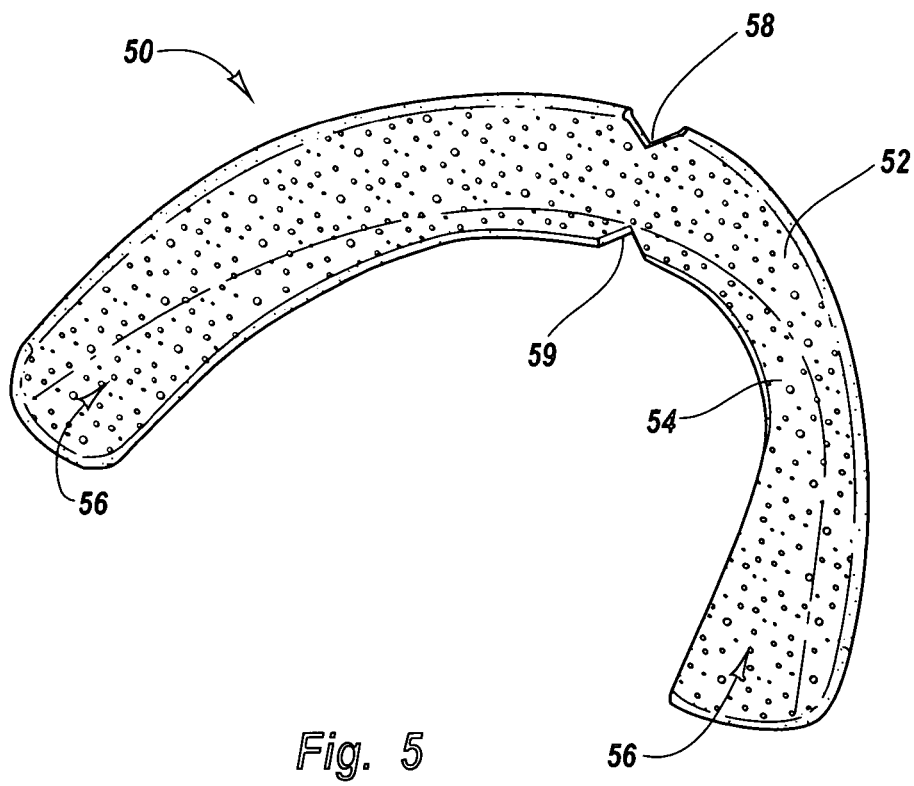
FIG. 5 is a perspective view of an exemplary medicament composition or treatment device having an L-shaped trough and a curved longitudinal profile.

FIG. 5 illustrates an alternative embodiment of a medicament composition or treatment device 50 according to the invention that is L-shaped. More particularly, the medicament composition or treatment device 50 includes a front side wall 52 and a rear side wall 54 extending laterally from the front side wall 52 so as to form a trough 56 having an approximate L-shaped cross section. The L-shaped medicament composition or treatment device 50 of FIG. 5 is somewhat easier to initially place over a person's dental arch compared to the U-shaped medicament compositions or treatment devices of FIGS. 1–4. This is due to the approximately planar orientation of the rear side wall 54 relative to the occlusal or incisal edges of a person's teeth when the front side wall 52 of the medicament composition or treatment device 50 is initially placed and adhered against the front surfaces of a person's teeth and/or gingiva. On the other hand, more manipulation of an L-shaped treatment device is generally required to form and adhere the rear side wall 54 against the lingual surfaces of the person's teeth and/or gingiva as a result of the greater initial offset angle between the front side wall 52 and rear side wall 54. However, the ability of medicament compositions and treatment devices according to the invention to adhere to tooth and/or gingival surfaces almost immediately, or within a few seconds, after being wetted facilitates the process of conforming the front side wall 52 and rear side wall 54 to the person's tooth and/or gingival surfaces.

In the case of the medicament composition or treatment device 50 having an L-shaped cross section, it may be more correct to say that the rear side wall 54 extending laterally from the front side wall 52 is really a bottom wall rather than a rear side wall. Nevertheless, because this "bottom wall" of an L-shaped medicament composition or treatment device is folded back against the lingual tooth and/or gingival surfaces during use, it can be readily seen that a medicament composition or treatment device having an L-shaped trough is merely a variation of a composition or treatment device having a V-shaped trough. Thus, for purposes of this disclosure and the appended claims, the side wall 54 shall constitute, and fall within the definition of, a "rear side wall".

To facilitate the ability of a medicament composition or treatment device to conform to the varying shapes and sizes among dental arches, the composition or device may include mechanical features such as one or more notches within the front or rear side walls. As shown in FIG. 5, the medicament composition or treatment device 50 includes a notch 58 in an outer edge near the center of the front side wall 52 and a notch 59 in an outer edge near the center of the rear side wall 54. Notches 58 and 59 allow the tray-like medicament composition or treatment device to more easily spread open or compress when being conformed to differently-sized dental arches. In this way, the medicament composition or treatment device 50 can more easily be a "one-size fits all" device.

Figure 6:
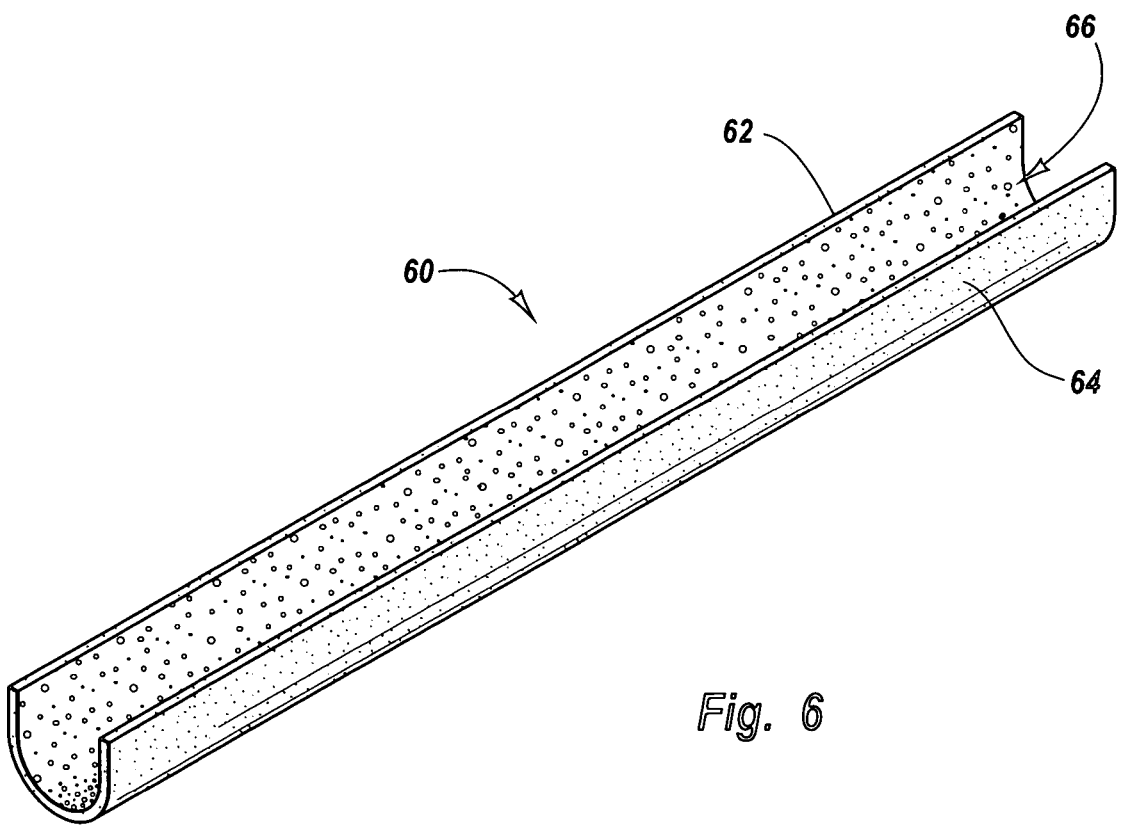
FIG. 6 is a perspective view of an exemplary medicament composition or treatment device having a U-shaped trough and a substantially straight longitudinal profile.

FIG. 6 depicts an alternative embodiment of a medicament composition or treatment device 60 according to the invention, which includes a front side wall 62 and a rear side wall 64 that define a U-shaped trough 66. Instead of being horseshoe shaped like the medicament compositions or treatment device of FIGS. 1–5, or otherwise having a curved longitudinal profile, the medicament composition or treatment device 60 of FIG. 6 has a substantially straight or linear longitudinal profile.

Figure 7:
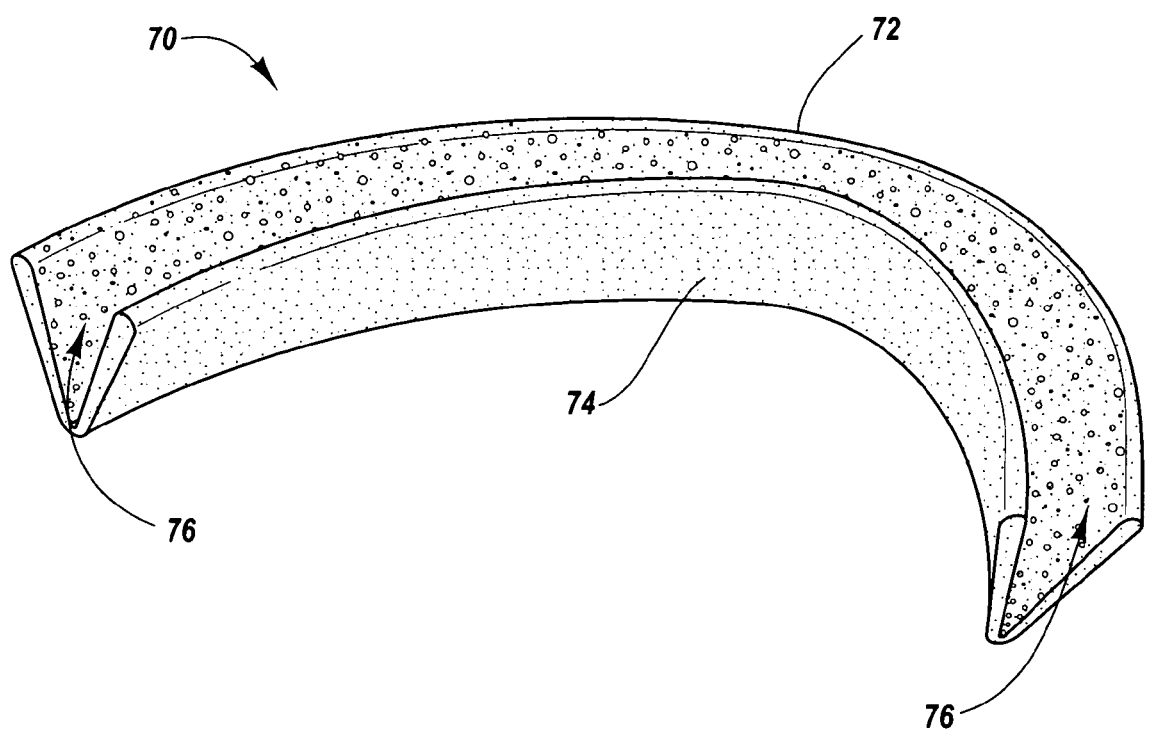
FIG. 7 is a perspective view of an exemplary medicament composition or treatment device having a V-shaped trough and a curved longitudinal profile.

FIG. 7 depicts yet another alternative embodiment of a medicament composition or treatment device 70 according to the invention. The medicament composition or treatment device 70 includes a front side wall 72 and a rear side wall 74 that define a V-shaped trough 76 and a curved longitudinal profile. The main difference between the V-shaped medicament composition or treatment device 70 of FIG. 7 and the L-shaped medicament composition or treatment device 50 of FIG. 5 is the angle at which the front and rear side walls are laterally offset from each other.

Notwithstanding the foregoing examples, it will be appreciated that medicament compositions and treatment devices according to the invention can have any longitudinal shape (e.g., they can have a straight or curved longitudinal profile from one end to the other). The front and rear side walls may define a trough of any desired cross-sectional shape (e.g., the trough can be trapezoidal, rectangular, or any other desired geometric shape).

The size and shape of medicament compositions according to the invention, as well as treatment devices incorporating such compositions, can be tailored to more readily fit either a person's upper dental arch or lower dental arch. They can be sized so as to treat all or merely a subset of a person's teeth and/or gingiva. The medicament composition or treatment device may be sufficiently adhesive and flexible so as to readily conform to a wide variety of differently-sized teeth, gingival areas, and dental arches. The medicament compositions or treatment devices are advantageously designed so as to substantially cover the front and lingual surfaces of the teeth and/or gingiva to be treated. Treating both surfaces yields a more even treatment, although it is certainly within the scope of the invention to treat one surface or more of one surface than another.

In general, the thickness of the barrier layer and/or the medicament composition within a treatment device can be adjusted to yield a dental treatment device having a desired strength and flexibility. In order for the barrier layer to remain flexible so as to conform to a person's teeth and/or gingiva, the barrier layer will preferably have a thickness ranging from about 0.025 mm to about 1.5 mm, more preferably in a range of about 0.5 mm to about 1.25 mm, and most preferably in a range of about 0.1 mm to about 1 mm.

The shaped medicament composition or layer will generally have a thickness ranging from about 0.1 mm to about 3 mm. The thickness of the medicament composition or layer can also be selected depending on the intended duration of each medicating session. In general, increasing the thickness of the medicament composition or layer will provide a longer or more sustained release of the active medicament(s). By way of example, for short wear times, the medicament composition will preferably have a thickness ranging from about 0.1 mm to about 0.5 mm. For intermediate wear times, the shaped medicament composition will preferably have a thickness ranging from about 0.5 mm to about 2 mm. For overnight treatments, the shaped medicament composition will preferably have a thickness ranging from about 2 mm to about 3 mm.

III. Methods of Making Substantially Solid Medicament Compositions and Treatment Devices Incorporating Such Compositions According to one embodiment, the medicament composition or layer is made by first forming a flowable medicament composition that is later dried to form a substantially solid medicament composition or layer. This may be performed by heating or otherwise causing one or more volatile solvents to be driven off by evaporation, thus leaving behind a substantially solid medicament composition or layer. The drying process may be performed before or after the medicament composition or layer is placed into contact with a barrier layer.

According to one embodiment, substantially solidified medicament compositions and treatment devices can be made by spreading a flowable medicament composition onto the surface of a large or continuous polymeric sheet (e.g., using a screeding device). The polymeric sheet and medicament composition are then placed into a forced air oven or other appropriate desiccation device in order to heat and drive off a substantial portion of the water or other solvent used to form the flowable medicament composition. Removal of the volatile solvent yields a medicament layer comprising a substantially solid medicament composition. Thereafter, individual tray-like treatment devices can be molded, such as by vacuum forming, pressing or stamping from the coated polymeric sheet and then separated into individual treatment devices suitable for placement over a person's teeth and/or gingiva.

Alternatively, the substantially solid medicament composition can be separated from the polymeric sheet and then molded, stamped or otherwise formed into a desired shape of a medicament composition.

Alternatively, a flowable or substantially solid medicament composition can be molded or shaped into a desired tray-like configuration comprising the medicament composition or layer. Thereafter, a barrier layer may optionally be attached or applied to an outer surface of the shaped medicament composition or layer. In this embodiment, the barrier layer may comprise a solid polymeric sheet or other barrier material, or it may initially comprise a flowable barrier material or precursor that is later cured or hardened, such as by removing a solvent by evaporation, by chemical or light curing, or by cooling a thermoplastic melt.

In yet another embodiment of the invention, a barrier layer in the form of a dental tray or tray-like device (e.g., a customized or non-custom tray) can be coated with a flowable medicament composition. The medicament composition is then heated together with the dental tray or otherwise allowed to dry in order to form a shaped medicament layer comprising a substantially solid medicament composition. This process can be performed during commercial manufacture of the treatment device or by an end user.

IV. Methods of Using Medicament Compositions and Treatment Devices Incorporating Such Compositions The medicament compositions according to the invention, as well as treatment devices incorporating such compositions, can be designed to be worn for any desired time period. Increasing the concentration of medicament generally reduces the treatment time required to provide a desired medicating effect. Nevertheless, due to the extremely comfortable fit and reliable adhesion between the inventive medicament compositions or treatment devices and the person's teeth and/or gingiva, it is possible to wear such compositions or devices for extended periods of time in order to ensure more uniform treatment. They may be designed to be worn while performing normal daily activities, such as talking, eating, drinking, smoking, coughing, smiling, frowning, grimacing, or while sleeping. This greatly decreases their intrusiveness into everyday activities compared to, e.g, conventional bleaching strips, which do not reliably adhere to teeth and/or gingiva, or intrusive devices such as large, bulky dental appliances.

Medicament compositions or treatment devices according to the invention may be worn over a person's upper dental arch, lower dental arch, or both simultaneously. The ability to reliably and comfortably wear medicament compositions or treatment devices over the upper and lower dental arches simultaneously is another departure from bleaching strips, which are not recommended for use in the upper and lower dental arches at the same time.

Figure 8:
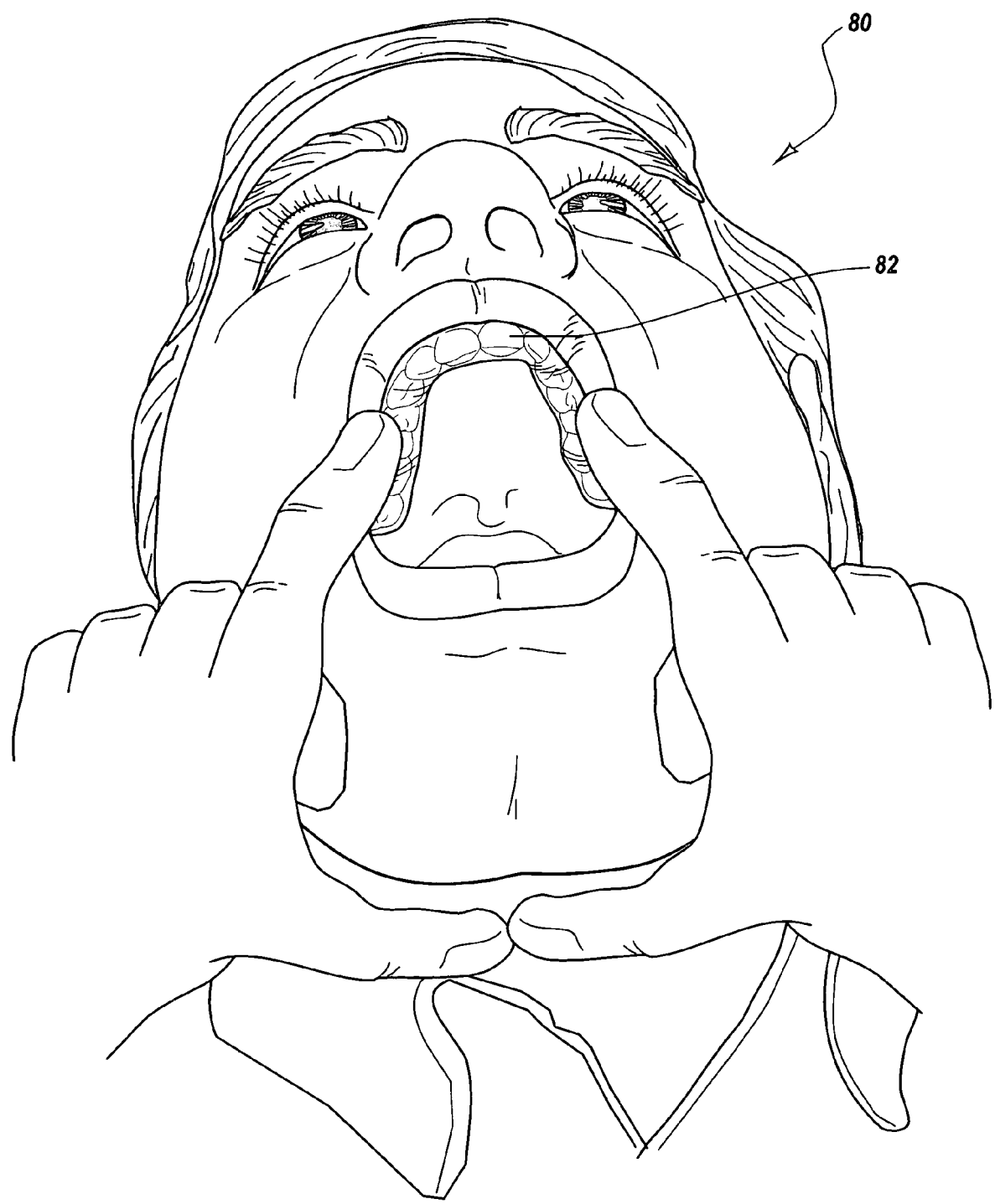
FIG. 8 illustrates a person placing a medicament composition or treatment device according to the invention over the upper dental arch.
Figure 9:
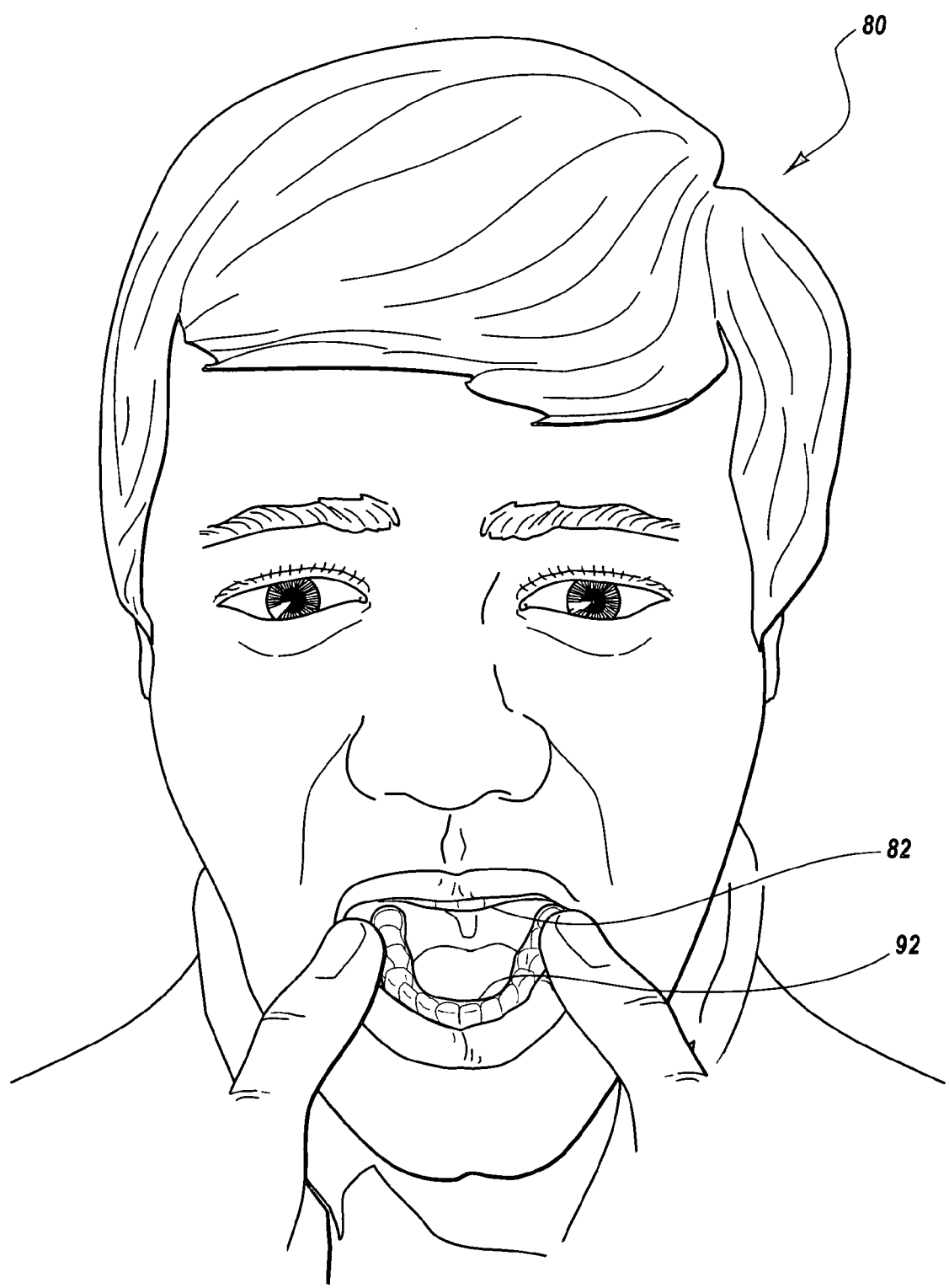
FIG. 9 illustrates a person placing a medicament composition or treatment device according to the invention over the lower dental arch, with a medicament composition or treatment device already placed over the upper dental arch.

FIG. 8 illustrates a person 80 placing a medicament composition or treatment device 82 over the person's upper dental arch. FIG. 9 illustrates the person 80 placing a medicament composition or treatment device 92 over the person's lower dental arch after having placed the medicament composition or treatment device 82 over the upper dental arch. It will be appreciated, however, that the medicament compositions or treatment devices can be placed over a person's upper and lower dental arches in any desired order.

To remove the medicament composition or treatment device, a user can pry open a corner of the barrier layer or medicament composition using a fingernail or rigid tool and then pull the remainder off. Any residual medicament composition or layer that remains adhered to the person's teeth and/or gingiva can be removed by washing, flushing water over, or by brushing the person's teeth and/or gingiva. Although medicament compositions are very adhesive to teeth and/or gingiva when protected from excessive moisture, they can be formulated to quickly break down and dissolve when flushed with excess water and/or by gentle mechanical action (e.g., brushing).

The medicament compositions or treatment devices can be worn for as little as a few minutes and as long as several hours. By way of example, not limitation, a typical treatment session of short duration may last from about 10 to about 30 minutes. A treatment session of intermediate duration may last from about 30 minutes to about 2 hours. A treatment session of long duration, including an overnight treatment while a person is sleeping, may last from about 2 hours to about 12 hours.

Treatment sessions may be repeated as many times as are needed to obtain a desired degree of medication. In some cases, a clinical effect has been observed after only 1–3 treatment sessions. A typical medicament regimen will preferably include 1–20 treatment sessions, more preferably 2–15 treatment sessions, and most preferably 3–10 treatment sessions.

The medicament compositions or treatment devices according to the invention may be used in conjunction with a dental bleaching regimen. The dental bleaching composition may be in the form of a gel (e.g., that is placed into a custom or non-custom tray), a bleaching strip (e.g., that is coated with a bleaching gel), or a substantially solid bleaching composition in the shape of a tray or tray-like device. Examples of suitable bleaching compositions in the form of a tray or tray-like shape are disclosed in copending U.S. application Ser. Nos. 10/446,235 and 10/446,741, both of which were filed May 27, 2003 and which were previously incorporated by reference.

The medicament compositions or treatment devices according to the invention may also be used in conjunction with a dental desensitizing regimen. The dental desensitizing composition may be in the form of a gel (e.g., that is placed into a custom or non-custom tray), a bleaching strip (e.g., that is coated with a bleaching gel), or a substantially solid desensitizing composition in the shape of a tray or tray-like device. Examples of suitable desensitizing compositions in the form of a tray or tray-like shape are disclosed in copending U.S. application Ser. No. 10/637,237, filed Aug. 8, 2003, and which was previously incorporated by reference.

V. Medicament Treatment Kits

For convenience of use, multiple medicament compositions or treatment devices may be packaged together and sold as a kit. In one embodiment, the number of medicament compositions or treatment devices provided with each kit will equal the number of treatment sessions that represent a prescribed medicament treatment regimen. Because of the ease of placing the inventive medicament compositions or treatment devices over a person's teeth and/or gingiva, coupled with the reliability with which they adhere to teeth and/or gingiva, the likelihood that a particular medicament composition or treatment device will not work as intended or fail is greatly decreased compared to (e.g., conventional bleaching strips).

To efficiently utilize the space within a kit package, multiple medicament compositions or treatment devices can be stacked or interested together. The medicament compositions or treatment devices can be sealed collectively or individually as desired. A protective package 30 is depicted in FIG. 3. The medicament composition or layer may optionally contain a removable protective layer on an interior surface to protect the medicament composition or layer from contamination or moisture.

It is within the scope of the invention to provide barrier layers and shaped medicament compositions that are initially separate and that are brought together by the end user. For example, the shaped medicament compositions may be a substantially solid insert that is placed into a customized or non-custom tray, that is coated with an initial flowable barrier material, or that is covered with a flexible barrier sheet. Alternatively, a flowable medicament composition can be placed within the trough of a tray-like barrier layer and allowed to solidify so as to yield a shaped medicament composition or layer.

The medicament compositions or treatment devices according to the invention may be used in conjunction with a dental bleaching regimen. In such a case, it may be desirable to provide a kit that includes one or more medicament compositions or treatment devices and one or more dental bleaching compositions or devices. The dental bleaching composition may be in the form of a gel (e.g., that is placed into a custom or non-custom tray), a bleaching strip (e.g., that is coated with a bleaching gel), or a substantially solid bleaching composition or device in the shape of a tray or tray-like device. Examples of suitable bleaching compositions and devices in the form of a tray or tray-like shape are disclosed in copending U.S. application Ser. Nos. 10/446,235 and 10/446,741, both of which were filed May 27, 2003, and which were previously incorporated by reference.

The medicament devices or compositions according to the invention may also be used in conjunction with a dental desensitizing regimen. In such a case, it may be desirable to provide a kit that includes one or more medicament compositions or treatment devices and one or more dental desensitizing compositions or devices. The dental desensitizing composition may be in the form of a gel (e.g., that is placed into a custom or non-custom tray), a desensitizing (e.g., that is coated with a desensitizing gel), or a substantially solid desensitizing composition or device in the shape of a tray or tray-like device. Examples of suitable desensitizing compositions and devices in the form of a tray or tray-like shape are disclosed in copending U.S. application Ser. No. 10/637,237, filed Aug. 8, 2003, which was previously incorporated by reference.

VI. Examples of the Preferred Embodiments

The following are several examples of medicament compositions and treatment devices that have been formulated and manufactured according to the invention. Such exemplary formulations and manufacturing conditions are given by way of example, and not by limitation, in order to illustrate medicament compositions and treatment devices that have been found to be useful for treating a person's teeth and/or gingiva. Unless otherwise indicated, all percentages are by weight.

EXAMPLE 1

An initially flowable medicament composition suitable for use in manufacturing a substantially solid, cohesive, and non-flowable medicament composition was formed by mixing together the following components:

| | |
|---|---|
| Chlorhexidine Gluconate | 2% |
| Polyvinyl pyrrolidone (M.W. = 1.3 million) | 30% |
| Ethanol | 33% |
| Water | 35% |

The resulting medicament composition was spread over the surfaces of three types of flexible polymer sheets: polyethylene sheets having a thickness of approximately 0.15 to 0.18 mm; sheets made of paraffin having a thickness of approximately 0.05 to 0.08 mm; and MYLAR sheets having a thickness of approximately 0.38 mm. The medicament composition was spread using a screeding device. The coated sheets were heated in a forced air oven heated to a temperature of 50–70° C. for approximately 1 hour. The coated sheets were removed from the oven and inspected. The medicament composition had dried sufficiently so as to form a solid, coherent medicament layer on the surface of the polymer sheets. The dried medicament composition adhered well to each of the polymer sheets.

The coated sheets were removed from the oven a second time, cut apart into smaller-sized pieces, and shaped into tray-like medicament treatment devices suitable for placement over a person's teeth and/or gingiva. The tray-like treatment devices included front and rear side walls that defined a trough having an approximate U- or V-shaped cross section and were curved in the longitudinal dimension to roughly approximate the curvature of a dental arch.

The tray-like treatment devices were tested by placing them over a person's teeth and/or gingiva. The residual saliva present on the tooth and/or gingival surfaces moistened the exposed surface of the dry medicament composition and caused it to become sticky and very adhesive to teeth and/or gingiva almost immediately. The medicament devices were pressed against the teeth and/or gingiva, which caused them to conform to the natural irregularities of the dental arch and adhere firmly against the teeth and/or gingival surfaces.

The tray-like dental medicament treatment devices were worn for varying time periods ranging from several minutes to several hours without becoming dislodged. Such devices are suitable for use in treating periodontal disease and other infections of oral tissues that respond to topical applications of antimicrobial compositions such as chlorhexidine gluconate.

EXAMPLE 2

An initially flowable medicament composition suitable for use in manufacturing a substantially solid, cohesive, and non-flowable medicament composition was formed by mixing together the following components:

| | |
|---|---|
| Cetylpyridinium Chloride | 2% |
| Ethanol | 28% |
| Polyvinyl pyrrolidone (M.W. = 1.3 million) | 35% |
| Water | 35% |

The resulting medicament composition was manufactured into substantially solid medicament compositions, as well as treatment devices incorporating such compositions, according to the method described in Example 1. The dried medicament composition adhered well to the barrier layers comprising polymer sheets.

The tray-like medicament devices were tested by placing them over a person's teeth and/or gingiva. The residual saliva present on the tooth and/or gingival surfaces moistened the exposed surface of the dry medicament composition and caused it to become sticky and very adhesive to teeth and/or gingiva almost immediately. The medicament devices were pressed against the teeth and/or gingiva, which caused them to conform to the natural irregularities of the dental arch and adhere firmly against the teeth and/or gingiva.

The tray-like dental medicament treatment devices were worn for varying time periods ranging from several minutes to several hours without becoming dislodged. Such devices are suitable for use in treating periodontal disease and other infections of oral tissues that respond to topical applications of anti-microbial compositions such as cetalpyridinium chloride.

EXAMPLE 3

An initially flowable medicament composition suitable for use in manufacturing a substantially solid, cohesive, and non-flowable medicament composition was formed by mixing together the following components:

| | |
|---|---|
| Phenol | 3% |
| Polyvinyl pyrrolidone (M.W. = 1.3 million) | 35% |
| Ethanol | 62% |

The resulting medicament composition was manufactured into substantially solid medicament compositions, as well as treatment devices incorporating such compositions, according to the method described in Example 1. The dried medicament composition adhered well to the barrier layers comprising polymer sheets.

The tray-like medicament devices were tested by placing them over a person's teeth and/or gingiva. The residual saliva present on the tooth and/or gingival surfaces moistened the exposed surface of the dry medicament composition and caused it to become sticky and very adhesive to teeth and/or gingiva almost immediately. The medicament devices were pressed against the teeth and/or gingiva, which caused them to conform to the natural irregularities of the dental arch and adhere firmly against the teeth and/or gingiva.

The tray-like medicament treatment devices were worn for varying time periods ranging from several minutes to several hours without becoming dislodged. Such devices are suitable for use in treating gingival infections and inflammation that responds to phenol.

EXAMPLE 4

An initially flowable remineralization composition suitable for use in manufacturing a substantially solid, cohesive, and non-flowable dental remineralizing composition was formed by mixing together the following components:

| | |
|---|---|
| Potassium Nitrate | 0.5% |
| Sodium Flouride | 0.25% |
| Polyvinyl pyrrolidone (M.W. = 1.3 million) | 32% |
| Ethanol | 30% |
| Water | 37.25% |

The resulting remineralizing composition was manufactured into substantially solid remineralizing compositions, as well as remineralizing devices incorporating such compositions according to the method described in Example 1. The dried remineralizing composition adhered well to the barrier layers comprising polymer sheets.

The tray-like remineralizing devices were tested by placing them over a person's teeth and/or gingiva. The residual saliva present on the tooth surfaces moistened the exposed surface of the solid remineralizing composition and caused it to become sticky and very adhesive to teeth almost immediately. The remineralizing devices were pressed against the teeth, which caused them to conform to the natural irregularities of the dental arch and adhere firmly against the teeth.

The tray-like dental remineralizing devices were worn for varying time periods ranging from several minutes to several hours without becoming dislodged. Such devices are suitable for preventing caries as a result of the remineralization effect of the sodium fluoride, as well as desensitizing sensitive teeth as a result of the potassium nitrate.

EXAMPLE 5

An initially flowable tooth remineralizing and bleaching composition suitable for use in manufacturing a substantially solid, cohesive, and non-flowable tooth remineralizing and bleaching composition was formed by mixing together the following components:

| | |
|---|---|
| Potassium Nitrate | 0.5% |
| Sodium Flouride | 0.25% |
| Carbamide Peroxide | 15% |
| Polyvinyl pyrrolidone (M.W. = 1.3 million) | 33% |
| Water | 51.25% |

The resulting composition was manufactured into tooth remineralizing and bleaching compositions and devices according to the method described in Example 1. The dried composition adhered well to the barrier layers comprising polymer sheets.

The tray-like treatment devices were tested by placing them over a person's teeth. The residual saliva present on the tooth surfaces moistened the exposed surface of the solid remineralizing/bleaching composition and caused it to become sticky and very adhesive to teeth almost immediately. The remineralizing and bleaching devices were pressed against the teeth, which caused them to conform to the natural irregularities of the dental arch and adhere firmly against the teeth.

The tray-like devices were worn for varying time periods ranging from several minutes to several hours without becoming dislodged.

The following hypothetical examples are given in order to more fully define the invention. While these examples are hypothetical in nature, they are based on actual mix designs that have been made and tested.

EXAMPLE 6

An initially flowable medicament composition suitable for use in manufacturing a substantially solid, cohesive, and non-flowable medicament composition is formed by mixing together the following components:

| | |
|---|---|
| Medicament | 16% |
| Polyvinyl pyrrolidone (M.W. = 1.3 million) | 38% |
| Water | 46% |

The medicament may be any known medicament, including those disclosed herein. The resulting medicament composition is manufactured into medicament devices according to the method described in Example 1. The dried medicament composition adheres well to the barrier layers comprising polymer sheets. The medicament devices can be used to treat a person's teeth and/or gingiva.

EXAMPLE 7

An initially flowable medicament composition suitable for use in manufacturing a substantially solid, cohesive, and non-flowable medicament composition is formed by mixing together the following components:

| | |
|---|---|
| Medicament | 16% |
| PolyOx WSR 101 (M.W. = 1 million) | 7% |
| Water | 77% |

The medicament may be any known medicament, including those disclosed herein. The resulting medicament composition is manufactured into medicament devices according to the method described in Example 1. The dried medicament composition does not adhere strongly to the polymer sheets but is easily separated from the sheets. The medicament devices can be used to treat a person's teeth and/or gingiva.

EXAMPLE 8

An initially flowable medicament composition suitable for use in manufacturing a substantially solid, cohesive, and non-flowable medicament composition is formed by mixing together the following components:

| | |
|---|---|
| Medicament | 16% |
| Carbopol 974P | 5% |
| Aqueous NaOH (50%) | 6% |
| Water | 73% |

The medicament may be any known medicament, including those disclosed herein. The resulting medicament composition is manufactured into medicament devices according to the method described in Example 1. Although the medicament composition is able to dry sufficiently to form a solid, it tends to shrink due to the large amount of water needed to cause Carbopol to form a gel. The medicament devices can be used to treat a person's teeth and/or gingiva, although they do not adhere as readily to a person's teeth and/or gingiva compared to compositions that use PVP or polyethylene oxide.

EXAMPLE 9

An initially flowable medicament composition suitable for use in manufacturing a substantially solid, cohesive, and non-flowable medicament composition is formed by mixing together the following components:

| | |
|---|---|
| Polyethylene Oxide (M.W. = 100,000) | 20% |
| Glycerin | 2.5% |
| Medicament | 2.4% |
| Water | 75.1% |

The medicament may be any known medicament, including those disclosed herein. The resulting medicament composition is manufactured into medicament devices according to the method described in Example 1. The dried medicament composition does not adhere strongly to the polymer sheets but is easily separated from the sheets. The medicament devices can be used to treat a person's teeth and/or gingiva. Thus, while polyethylene oxide is a satisfactory adhesion agent, it is less satisfactory in promoting adhesion between a dried medicament composition and a polymer sheet.

EXAMPLE 10

An initially flowable medicament composition suitable for use in manufacturing a substantially solid, cohesive, and non-flowable medicament composition is formed by mixing together the following components:

| | |
|---|---|
| Medicament | 10% |
| Water | 25% |
| Ethanol | 25% |
| Polyvinyl pyrrolidone (M.W. = 1.3 million) | 38% |
| Glycerin | 73% |

The medicament may be any known medicament, including those disclosed herein. The resulting medicament composition is manufactured into medicament devices according to the method described in Example 1. Using a mixture of water and ethanol as the solvent allows the medicament composition to dry in less than time than the compositions that use water as the only solvent. The inclusion of glycerin helps the medicament composition remain more flexible and less brittle after drying. The dried medicament composition adheres well to the barrier layers comprising polymer sheets. The medicament devices can be used to treat a person's teeth and/or gingiva.

EXAMPLE 11

An initially flowable medicament composition suitable for use in manufacturing a substantially solid, cohesive, and non-flowable medicament composition is formed by mixing together the following components:

| | |
|---|---|
| Medicament | 10% |
| Water | 21% |
| Ethanol | 21% |
| Kollidon VA 64 (M.W. = 60,000) | 40% |
| Carboxy methyl cellulose | 3% |
| PEG 600 | 5% |

Kollidon VA 64 is a polyvinyl pyrrolidone polymer sold by BASF. The medicament may be any known medicament, including those disclosed herein. The resulting medicament composition is manufactured into medicament devices according to the method described in Example 1. Using a mixture of water and ethanol as the solvent allows the medicament composition to dry in less than time than the compositions that use water as the only solvent. The inclusion of PEG helps the medicament composition remain more flexible and less brittle after drying. The dried medicament composition adheres well to the barrier layers comprising polymer sheets. The medicament devices can be used to treat a person's teeth and/or gingiva.

EXAMPLE 12

An initially flowable medicament composition suitable for use in manufacturing a substantially solid, cohesive, and non-flowable medicament composition is formed by mixing together the following components:

| | |
|---|---|
| Medicament | 11.6% |
| Ethanol | 55.8% |
| Kollidon VA 90 F (M.W. = 1.3 million) | 24.4% |
| Carboxy methyl cellulose | 2.3% |
| PEG 600 | 5.8% |

The medicament may be any known medicament, including those disclosed herein. The resulting medicament composition is manufactured into medicament devices according to the method described in Example 1. Using ethanol as the only solvent allows the medicament composition to dry in even less time than compositions that use a mixture of water and ethanol as the only solvent. The inclusion of PEG helps the medicament composition remain more flexible and less brittle after drying. The dried medicament composition adheres well to the barrier layers comprising polymer sheets. The medicament devices can be used to treat a person's teeth and/or gingiva.

EXAMPLE 13

An initially flowable medicament composition suitable for use in manufacturing a substantially solid, cohesive, and non-flowable medicament composition is formed by mixing together the following components:

| | |
|---|---|
| Medicament | 10% |
| Ethanol | 65% |
| Kollidon VA 90 F (M.W. = 1.3 million) | 20% |
| PEG 600 | 5% |

The medicament may be any known medicament, including those disclosed herein. The resulting medicament composition is manufactured into medicament devices according to the method described in Example 1. Using ethanol as the only solvent allows the medicament composition to dry in even less time than compositions that use a mixture of water and ethanol as the only solvent. The inclusion of PEG helps the medicament composition remain more flexible and less brittle after drying. The dried medicament composition adheres well to the barrier layers comprising polymer sheets. The medicament devices can be used to treat a person's teeth and/or gingiva.

EXAMPLE 14

An initially flowable medicament composition suitable for use in manufacturing a substantially solid, cohesive, and non-flowable medicament composition is formed by mixing together the following components:

| | |
|---|---|
| Medicament | 10% |
| Ethanol | 64% |
| Kollidon VA 90 F (M.W. = 1.3 million) | 25% |
| PEG 600 | 1% |

The medicament may be any known medicament, including those disclosed herein. The resulting medicament composition is manufactured into medicament devices according to the method described in Example 1. Using ethanol as the only solvent allows the medicament composition to dry in even less time than compositions that use a mixture of water and ethanol as the only solvent. The inclusion of PEG helps the medicament composition remain more flexible and less brittle after drying. The dried medicament composition adheres well to the barrier layers comprising polymer sheets. The medicament devices can be used to treat a person's teeth and/or gingiva.

EXAMPLE 15

An initially flowable medicament composition suitable for use in manufacturing a substantially solid, cohesive, and non-flowable medicament composition is formed by mixing together the following components:

| | |
|---|---|
| Medicament | 10% |
| Ethanol | 64% |
| Kollidon VA 90 F (M.W. = 1.3 million) | 23% |
| PEG 600 | 1% |
| Aerosil 200 | 2% |

The medicament may be any known medicament, including those disclosed herein. The resulting medicament composition is manufactured into medicament devices according to the method described in Example 1. Using ethanol as the only solvent allows the medicament composition to dry in even less time than compositions that use a mixture of water and ethanol as the only solvent. The inclusion of PEG helps the medicament composition remain more flexible and less brittle after drying. Aerosil 200 is added as a tackifying agent to promote adhesion of the wet medicament composition to the polymer sheets. The dried medicament composition adheres well to the barrier layers comprising polymer sheets. The medicament devices can be used to treat a person's teeth and/or gingiva.

EXAMPLE 16

An initially flowable medicament composition suitable for use in manufacturing a substantially solid, cohesive, and non-flowable medicament composition is formed by mixing together the following components:

| Medicament | 10% |
|---|---|
| Ethanol | 66.9% |
| Kollidon VA 90 F (M.W. = 1.3 million) | 20% |
| PEG 600 | 0.1% |
| Aerosil 200 | 3% |

The medicament may be any known medicament, including those disclosed herein. The resulting medicament composition is manufactured into medicament devices according to the method described in Example 1. Using ethanol as the only solvent allows the medicament composition to dry in even less time than compositions that use a mixture of water and ethanol as the only solvent. Aerosil 200 is added as a tackifying agent to promote adhesion of the wet medicament composition to the polymer sheets. The dried medicament composition adheres well to the barrier layers comprising polymer sheets. The medicament devices can be used to treat a person's teeth and/or gingiva.

EXAMPLE 17

An initially flowable medicament composition suitable for use in manufacturing a substantially solid, cohesive, and non-flowable medicament composition is formed by mixing together the following components:

| Medicament | 10% |
|---|---|
| PolyOx (M.W. = 1 million) | 7.5% |
| Water | 75.5% |
| Glycerin | 5% |
| Aerosil 200 | 2% |

The medicament may be any known medicament, including those disclosed herein. The resulting medicament composition is manufactured into medicament devices according to the method described in Example 1. The inclusion of glycerin helps the medicament composition remain more flexible and less brittle after drying. The medicament composition does not adhere well to MYLAR sheets. It also shrinks somewhat after extended drying. The medicament devices can be used to treat a person's teeth and/or gingiva.

EXAMPLE 18

An initially flowable medicament composition suitable for use in manufacturing a substantially solid, cohesive, and non-flowable medicament composition is formed by mixing together the following components:

| Medicament | 10% |
|---|---|
| Kollidon 90 F (M.W. = 1.3 million) | 10% |
| Kollidon 30 (M.W. = 50,000) | 20% |
| Water | 53% |
| Glycerin | 5% |
| Aerosil 200 | 2% |

The medicament may be any known medicament, including those disclosed herein. The resulting medicament composition is manufactured into medicament devices according to the method described in Example 1. The inclusion of glycerin helps the medicament composition remain more flexible and less brittle after drying. Aerosil 200 is added as a tackifying agent to promote adhesion of the wet medicament composition to the polymer sheets. The dried medicament composition adheres well to each of the polymer sheets. The medicament devices can be used to treat a person's teeth and/or gingiva.

EXAMPLE 19

An initially flowable medicament composition suitable for use in manufacturing a substantially solid, cohesive, and non-flowable medicament composition was formed by mixing together the following components:

| Medicament | 10% |
|---|---|
| Kollidon 90 F (M.W. = 1.3 million) | 27% |
| Water | 50% |
| Glycerin | 7% |
| Aerosil 200 | 6% |

The medicament may be any known medicament, including those disclosed herein. The resulting medicament composition is manufactured into medicament devices according to the method described in Example 1. The inclusion of glycerin helps the medicament composition remain more flexible and less brittle after drying. Aerosil 200 is added as a tackifying agent to promote adhesion of the wet medicament composition to the polymer sheets. The dried medicament composition adheres well to each of the polymer sheets. The medicament devices can be used to treat a person's teeth and/or gingiva.

EXAMPLE 20

An initially flowable medicament composition suitable for use in manufacturing a substantially solid, cohesive, and non-flowable medicament composition is formed by mixing together the following components:

| Medicament | 10% |
|---|---|
| Kollidon 90 F (M.W. = 1.3 million) | 28% |
| Water | 50% |
| Glycerin | 7% |
| Aerosil 200 | 5% |

The medicament may be any known medicament, including those disclosed herein. The resulting medicament composition is manufactured into medicament devices according to the method described in Example 1. The inclusion of glycerin helps the medicament composition remain more flexible and less brittle after drying. Aerosil 200 is added as a tackifying agent to promote adhesion of the wet medicament composition to the polymer sheets. The dried medicament composition adheres well to each of the polymer sheets. The medicament devices can be used to treat a person's teeth and/or gingiva.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. An article of manufacture for use in treating a person's teeth and/or gingiva, comprising:
    a substantially solid and coherent medicament composition having a tray-like configuration comprising a front side wall, a rear side wall, and a trough between said front and rear side walls,
    said medicament composition having a rigidity so as to maintain itself in the tray-like configuration absent external support,
    said medicament composition having increased adhesiveness to teeth and/or gingiva when moistened by saliva or water,
    said medicament composition comprising:
        at least one medicament; and
        at least one tissue adhesion agent that forms a substantially solid matrix within which said medicament is dispersed and that at least partially contributes to said increased adhesiveness to teeth and/or gingiva when said medicament composition is moistened by saliva or water.

2. An article of manufacture as defined in claim 1, said medicament composition being initially horseshoe shaped prior to use so that said medicament composition at least approximately conforms to a person's dental arch with minimal longitudinal shaping.

3. An article of manufacture as defined in claim 1, said medicament composition initially having a longitudinal curvature that is less than the curvature of a person's dental arch prior to use so that additional longitudinal curving of said medicament composition is required when said medicament composition is placed over a person's teeth and/or gingiva.

4. An article of manufacture as defined in claim 1, said medicament composition initially having a substantially straight longitudinal profile prior to use so that longitudinal curving of said medicament composition is required when said medicament composition is placed over a person's teeth and/or gingiva.

5. An article of manufacture as defined in claim 1, at least a portion of said trough having an approximate U-shaped cross section.

6. An article of manufacture as defined in claim 1, at least a portion of said trough having an approximate V-shaped cross section.

7. An article of manufacture as defined in claim 1, at least a portion of said trough having an approximate L-shaped cross section.

8. An article of manufacture as defined in claim 1, at least a portion of said trough having approximately a rectangular or trapezoidal cross section.

9. An article of manufacture as defined in claim 1, said medicament comprising at least one antimicrobial agent.

10. An article of manufacture as defined in claim 9, said antimicrobial agent comprising at least one of chlorhexidine gluconate, cetylpyridinium chloride, phenol, minocycline, tetracycline, doxycycline, penicillin, clindamycin, ciprofloxacin, metronidazole, or tricolsan.

11. An article of manufacture as defined in claim 1, said medicament comprising at least one remineralizing agent.

12. An article of manufacture as defined in claim 11, said remineralizing agent comprising at least one of a fluoride salt, sodium fluoride, sodium monofluorophosphate, stannous fluoride, or calcium phosphate.

13. An article of manufacture as defined in claim 1, said medicament comprising at least one anti-tartar agent.

14. An article of manufacture as defined in claim 13, said anti-tartar agent comprising at least one of pyrophosphate, polypyrophosphate, polyvinyl methyl ether malic acid, sodium hexametal phosphate, alkali metal phosphate, or calcium lactate.

15. An article of manufacture as defined in claim 1, said medicament comprising at least one of an anticalculus or antiplaque agent.

16. An article of manufacture as defined in claim 15, said anticalculus or antiplaque agent comprising at least one of 8-hydroxyquinoline sulfate, dicitrate cyclic ester, or zinc citrate.

17. An article of manufacture as defined in claim 1, said medicament having a concentration in a range of about 0.0 1% to about 50% by weight of said medicament composition.

18. An article of manufacture as defined in claim 1, said medicament having a concentration in a range of about 0.5% to about 25% by weight of said medicament composition.

19. An article of manufacture as defined in claim 1, said medicament having a concentration in a range of about 0.1% to about 10% by weight of said medicament composition.

20. An article of manufacture as defined in claim 1, said tissue adhesion agent comprising polyvinyl pyrrolidone.

21. An article of manufacture as defined in claim 1, said tissue adhesion agent comprising at least one of carboxypolymethylene, polyethylene oxide, polyacrylic acid, copolymer of polyacrylic acid, polyacrylate, polyacrylamide, copolymer of polyacrylic acid and polyacrylamide, PVP-vinyl acetate copolymer, carboxymethylcellulose, carboxypropylcellulose, polysaccharide gum, or protein.

22. An article of manufacture as defined in claim 1, said tissue adhesion agent having a concentration in a range of about 10% to about 90% by weight of said medicament composition.

23. An article of manufacture as defined in claim 1, said tissue adhesion agent having a concentration in a range of about 20% to about 80% by weight of said medicament composition.

24. An article of manufacture as defined in claim 1, said tissue adhesion agent having a connection in a range of about 40% to about 75% by weight of said medicament composition.

25. An article of manufacture as defined in claim 1, said medicament composition further comprising at least one humectant.

26. An article of manufacture as defined in claim 1, wherein said medicament composition is sized and configured so as to fit over at least a portion of a person's upper dental arch.

27. An article of manufacture as defined in claim 1, wherein said medicament composition is sized and configured so as to fit over at least a portion of a person's lower dental arch.

28. An article of manufacture as defined in claim 1, wherein said medicament composition has a cross-sectional thickness in a range of about 0.1 mm to about 0.5 mm.

29. An article of manufacture as defined in claim 1, wherein said medicament composition has a cross-sectional thickness in a range of about 0.5 nun to about 2 mm.

30. An article of manufacture as defined in claim 1, wherein said medicament composition has a cross-sectional thickness in a range of about 2 mm to about 3 mm.

31. An article of manufacture as defined in claim 1, wherein said medicament composition is contained within a sealed package prior to use.

32. Art article of manufacture as defined in claim 1, further comprising a barrier layer comprising a moisture-resistant material adjacent to an outer surface of said medicament composition that protects the medicament composition from saliva or moisture when in use.

33. An article of manufacture as defined in claim 32, said barrier layer being flexible so that it will readily conform to the shape of a person's teeth and/or gingiva when in use.

34. An article of manufacture as defined in claim 32, said barrier layer comprising at least one polyolefin.

35. An article of manufacture as defined in claim 34, said polyolefin comprising at least one of polyethylene, high density polyethylene, low density polyethylene, ultra-low density polyethylene, polypropylene, or polytetrafluoroethylene.

36. An article of manufacture as defined in claim 34, said barrier layer comprising at least one of wax, metal foil, paraffin, ethylene-vinyl acetate copolymer, ethylene-vinyl alcohol copolymer, polycaprolactone, polyester, polycarbonate, polyurethane, polyamide, or polyesteramide.

37. An article of manufacture as defined in claim 1, said medicament composition further comprising at least one dental bleaching agent.

38. An article of manufacture as defined in claim 37, said dental bleaching agent having a concentration in a range of about 5% to about 80% by weight of said medicament composition.

39. An article of manufacture as defined in claim 37, said dental bleaching agent having a concentration in a range of about 10% to about 60% by weight of said medicament composition.

40. An article of manufacture as defined in claim 37, said dental bleaching agent having a concentration in a range of about 20% to about 50% by weight of said medicament composition.

41. An article of manufacture as defined in claim 1, said medicament composition further comprising at least one dental desensitizing agent.

42. A kit for use in medicament a person's teeth and/or gingiva comprising a plurality of substantially solid medicament compositions having a tray-like configuration according to claim 1.

43. A method for medicating a person's teeth and/or gingiva comprising obtaining a medicament composition according to claim 1 and then placing said medicament composition over at least a portion of the person's teeth and/or gingiva for a desired time period.

44. A method for medicating a person's teeth and/or gingiva as defined in claim 43, further comprising placing a barrier layer adjacent to an outer surface of said medicament composition.

45. An article of manufacture comprising a treatment device for use in treating a person's teeth and/or gingiva, said treatment device comprising:

a barrier layer comprising a moisture-resistant material in the shape of a dental tray comprising a front side wall, a rear side wall, and a trough between said front and rear side walls; and a medicament layer within said trough comprising a substantially solid medicament composition having a first surface adjacent to said barrier layer and a second surface that has increased adhesiveness to teeth and/or gingiva when moistened by saliva or water, said medicament layer being in the shape of a dental tray and having a rigidity so as to at least partially contribute to maintaining said treatment device in the shape of a dental tray prior to placing said treatment device over a person's teeth and/or gingiva, said medicament composition comprising:

at least one medicament; and at least one tissue adhesion agent that forms a substantially solid matrix within which said medicament is dispersed and that at least partially contributes to said increased adhesiveness to teeth and/or gingiva when said medicament composition is moistened by saliva or water.

46. An article of manufacture as defined in claim 45, at least a portion of said trough having a cross section that is approximately U-shaped, V-shaped, L-shaped, rectangular, or trapezoidal.

47. An article of manufacture as defined in claim 45, said barrier layer being flexible so that it will readily conform to the shape of a person's teeth and/or gingiva when in use.

48. An article of manufacture as defined in claim 45, said barrier layer comprising at least one polyolefin.

49. An article of manufacture as defined in claim 48, said polyolefin comprising at least one of polyethylene, high density polyethylene, low density polyethylene, ultra-low density polyethylene, polypropylene, or polytetrafluoroethylene.

50. An article of manufacture as defined in claim 45, said barrier layer comprising at least one of wax, metal foil, paraffin, ethylene-vinyl acetate copolymer, ethylene-vinyl alcohol copolymer, polycaprolactone, polyester, polycarbonate, polyurethane, polyamide, or polyesteramide.

51. An article of manufacture as defined in claim 45, said barrier layer having a rigidity so as to at least partially contribute to maintaining said medicament device in the shape of a dental tray prior to placing said medicament device over a person's teeth and/or gingiva.

52. An article of manufacture as defined in claim 45, said barrier layer being initially horseshoe shaped prior to use so that said medicament device at least approximately conforms to a person's dental arch with minimal longitudinal shaping.

53. An article of manufacture as defined in claim 45, said barrier layer initially having a longitudinal curvature that is less than the curvature of a person's dental arch prior to use so that additional longitudinal curving of said medicament device is required when said medicament device is placed over a person's teeth and/or gingiva.

54. An article of manufacture as defined in claim 45, said barrier layer initially having a substantially straight longitudinal profile prior to use so that longitudinal curving of said medicament device is required when said medicament device is placed over a person's teeth and/or gingiva.

55. An article of manufacture as defined in claim 45, said barrier layer comprising a customized dental tray.

56. An article of manufacture as defined in claim 45, said medicament layer comprising a single coherent mass in the shape of a dental tray comprising a front side wall, a rear side wall, and a trough between said front and rear side walls.

57. Art article of manufacture as defined in claim 45, said medicament comprising at least one member selected from chlorhexidine gluconate, cetylpyridinium chloride, phenol, minocycline, tetracycline, doxycycline, penicillin, clindamycin, ciprofloxacin, metronidazole, or tricolsan.

58. An article of manufacture as defined in claim 45, at least a portion of said tissue adhesion agent comprising polyvinyl pyrrolidone.

59. A kit for use in medicating a person's teeth and/or gingiva comprising a plurality of treatment devices according to claim 45.

60. A method for medicating a person's teeth and/or gingiva comprising obtaining a treatment device according to claim 45 and then placing said treatment device over at least a portion of the person's teeth and/or gingiva for a desired time period.

61. A method of manufacturing an article of manufacture comprising a substantially solid and coherent medicament composition, the method comprising:
  mixing together a medicament, a tissue adhesion agent and a solvent to form an intermediate flowable composition; and
  removing at least a portion of said solvent from said intermediate flowable composition so as to form said substantially solid and coherent medicament composition,
    said medicament composition having a tray-like configuration comprising a front side wall, a rear side wall, and a trough between said front and rear side walls.

62. A method of manufacturing an article of manufacture as defined in claim 61, further comprising forming a barrier layer adjacent to said medicament composition.

63. A method of manufacturing an article of manufacture as defined in claim 62, wherein said barrier layer comprises a dental tray.

64. A method of manufacturing an article of manufacture as defined in claim 63, said method comprising first placing said intermediate flowable composition adjacent to said dental tray prior and then removing at least a portion of said solvent from said intermediate flowable composition to form said substantially solid and coherent medicament composition.

65. A method of manufacturing an article of manufacture as defined in claim 63, said method comprising first forming said medicament composition having a tray-like configuration and then placing it inside a trough within said dental tray.

66. A method of manufacturing an article of manufacture as defined in claim 62, said method comprising applying an initially flowable material adjacent to said medicament composition and allowing the initially flowable material to solidify into a solid barrier layer.

67. A method of manufacturing an article of manufacture as defined in claim 62, said method comprising first placing said intermediate flowable composition adjacent to a polymeric sheet comprising said barrier layer, removing at least a portion of said solvent from said intermediate flowable composition to form a substantially solid and coherent medicament composition, and shaping said medicament composition and barrier layer into the tray-like configuration.

68. A method of manufacturing an article of manufacture as defined in claim 62, wherein said baffler layer comprises a single layer of a water-resistant polymeric material.

* * * * *

UNITED STATES PATENT AND TRADEMARK OFFICE
CERTIFICATE OF CORRECTION

| | |
|---|---|
| PATENT NO. | : 7,056,118 B2 |
| APPLICATION NO. | : 10/646484 |
| DATED | : June 6, 2006 |
| INVENTOR(S) | : Allred et al. |

It is certified that error appears in the above-identified patent and that said Letters Patent is hereby corrected as shown below:

Front Page
(54) Patent Title, after "CONFIGURATION FOR DELIVERING", change "A" to --AN ORAL--

Column 1
Line 3, after "DELIVERING", change "A" to --AN ORAL--

Column 18
Line 63, after "10/446,235 and", change "10/446,741" to --10/446,471--

Column 19
Line 59, after "235 and", change "10/446,741" to --10/446,471--

Column 25
Line 27, after "dry in less", remove "than"

Column 30
Line 54, after "having a", change "connection" to --concentration--

Column 31
Line 6, after "about 0.5", change "nun" to --mm--
Line 13, before "article of", change "Art" to --An--
Line 51, after "for use in", change "medicament" to --medicating--

Column 33
Line 4, before "article of", change "Art" to --An--

UNITED STATES PATENT AND TRADEMARK OFFICE
CERTIFICATE OF CORRECTION

PATENT NO. : 7,056,118 B2
APPLICATION NO. : 10/646484
DATED : June 6, 2006
INVENTOR(S) : Allred et al.

It is certified that error appears in the above-identified patent and that said Letters Patent is hereby corrected as shown below:

<u>Column 34</u>
Line 31, after "wherein said", change "baffler" to --barrier--

Signed and Sealed this

Fifth Day of December, 2006

JON W. DUDAS
*Director of the United States Patent and Trademark Office*